(12) United States Patent
Hancock et al.

(10) Patent No.: US 11,135,006 B2
(45) Date of Patent: Oct. 5, 2021

(54) ELECTROSURGICAL CUTTING TOOL

(71) Applicant: CREO MEDICAL LIMITED, Chepstow (GB)

(72) Inventors: Christopher Paul Hancock, Bath (GB); Louis Turner, Chepstow (GB); Malcolm White, Chepstow (GB); Sandra May Swain, Chepstow (GB); Patrick Burn, Chepstow (GB); Steven Morris, Chepstow (GB)

(73) Assignee: CREO MEDICAL LIMITED, Chepstow (GB)

(*) Notice: Subject to any disclaimer, the term of this patent is extended or adjusted under 35 U.S.C. 154(b) by 452 days.

(21) Appl. No.: 16/086,442

(22) PCT Filed: May 16, 2017

(86) PCT No.: PCT/EP2017/061740
§ 371 (c)(1),
(2) Date: Sep. 19, 2018

(87) PCT Pub. No.: WO2017/198671
PCT Pub. Date: Nov. 23, 2017

(65) Prior Publication Data
US 2019/0099215 A1    Apr. 4, 2019

(30) Foreign Application Priority Data
May 17, 2016 (GB) ...................... 1608679

(51) Int. Cl.
*A61B 18/12* (2006.01)
*A61B 18/18* (2006.01)
(Continued)

(52) U.S. Cl.
CPC ...... *A61B 18/1445* (2013.01); *A61B 18/1206* (2013.01); *A61B 18/1815* (2013.01);
(Continued)

(58) Field of Classification Search
CPC ............ A61B 18/1206; A61B 18/1445; A61B 18/1815; A61B 2018/00494;
(Continued)

(56) References Cited

U.S. PATENT DOCUMENTS 3,573,681 A    4/1971   Miller
5,312,434 A *  5/1994   Crainich ................ A61B 17/29
                                                   606/170
(Continued)

FOREIGN PATENT DOCUMENTS

CN    202554060 U    11/2012
CN    103327923 A     9/2013
(Continued)

OTHER PUBLICATIONS

The First Office Action, from the State Intellectual Property Office of People's Republic of China in counterpart Application No. 201780016473.2, dated Jul. 2, 2020.
(Continued)

*Primary Examiner* — Daniel W Fowler
(74) *Attorney, Agent, or Firm* — Arent Fox LLP

(57) ABSTRACT

An electrosurgical cutting tool comprising a pair of pivotable blades that are mechanically operable as scissors or pliers. The blades have electrodes capable of delivery RF and/or microwave energy to cut or coagulate tissue between them. The tool combines the actuation and energy delivery mechanisms in a compact arrangement that enables the tool to be inserted through an instrument channel of a surgical scoping device, such as an endoscope, gastroscope or laparoscope. Each blade may comprise a planar body made of dielectric material that separates a first conductive element from a second conductive element. The blades may rotate relative to each other in the plane of the blades.

26 Claims, 12 Drawing Sheets

(51) Int. Cl.
*A61B 18/14* (2006.01)
*A61B 18/00* (2006.01)

(52) U.S. Cl.
CPC ............ *A61B 2018/0016* (2013.01); *A61B 2018/0063* (2013.01); *A61B 2018/00083* (2013.01); *A61B 2018/00494* (2013.01); *A61B 2018/00589* (2013.01); *A61B 2018/00601* (2013.01); *A61B 2018/00607* (2013.01); *A61B 2018/00982* (2013.01); *A61B 2018/00994* (2013.01); *A61B 2018/124* (2013.01); *A61B 2018/1273* (2013.01); *A61B 2018/1861* (2013.01)

(58) Field of Classification Search
CPC .... A61B 2018/00589; A61B 2018/124; A61B 2018/1273; A61B 2018/1861
See application file for complete search history.

(56) References Cited

U.S. PATENT DOCUMENTS

| | | | | |
|---|---|---|---|---|
| 5,318,589 | A * | 6/1994 | Lichtman | A61B 17/29 600/564 |
| 5,766,166 | A * | 6/1998 | Hooven | A61B 18/1445 606/45 |
| 5,784,034 | A | 7/1998 | Konishi et al. | |
| 5,909,196 | A | 6/1999 | O'Neill, Jr. | |
| 6,075,501 | A | 6/2000 | Kuramoto et al. | |
| 6,193,718 | B1 | 2/2001 | Kortenbach et al. | |
| 2004/0087940 | A1 * | 5/2004 | Jahns | A61B 18/1445 606/41 |
| 2004/0087943 | A1 * | 5/2004 | Dycus | A61B 17/2909 606/51 |
| 2004/0243004 | A1 * | 12/2004 | Carr | A61B 5/0507 600/467 |
| 2008/0015566 | A1 * | 1/2008 | Livneh | A61B 17/295 606/37 |
| 2009/0306647 | A1 * | 12/2009 | Leyh | A61B 18/1233 606/34 |
| 2010/0057071 | A1 | 3/2010 | Amoah et al. | |
| 2012/0053577 | A1 * | 3/2012 | Lee | A61B 18/1815 606/33 |
| 2013/0274733 | A1 * | 10/2013 | Hancock | A61B 18/1445 606/33 |

FOREIGN PATENT DOCUMENTS

| | | |
|---|---|---|
| EP | 2 233 098 A1 | 9/2010 |
| EP | 2 335 632 A2 | 6/2011 |
| EP | 2 436 328 A1 | 4/2012 |
| EP | 2 556 794 A1 | 2/2013 |
| GB | 2487288 A | 7/2012 |
| WO | WO 90/06079 A1 | 6/1990 |
| WO | WO 94/11059 A1 | 5/1994 |
| WO | WO 96/27338 A1 | 9/1996 |
| WO | WO 2004/045442 A1 | 6/2004 |

OTHER PUBLICATIONS

International Search Report for PCT/EP2017/061740 dated May 16, 2017.

Search Report in United Kingdom Application No. GB 1608872.6 dated Jul. 15, 2016.

* cited by examiner

ELECTROSURGICAL CUTTING TOOL

CROSS-REFERENCE TO RELATED APPLICATIONS

This application is a National Stage entry of International Application No. PCT/EP2017/061740, filed on May 16, 2017, which claims priority to United Kingdom Patent Application No. 1608679.5, filed on May 17, 2016. The disclosures of the priority applications are incorporated in their entirety herein by reference.

FIELD OF THE INVENTION

The invention relates to an electrosurgical cutting and coagulation tool, for cutting and coagulating biological tissue. In particular the invention relates to an electrosurgical cutting tool capable of delivering radiofrequency (RF) energy for cutting biological tissue and/or microwave frequency energy for haemostasis (i.e. sealing broken blood vessels by promoting coagulation of blood).

BACKGROUND TO THE INVENTION

Surgical resection is a means of removing sections of organs from within the human or animal body. The organs may be highly vascular. When tissue is cut (i.e. divided or transected), small blood vessels may be damaged or ruptured. Initial bleeding is followed by a coagulation cascade where the blood is turned into a clot in an attempt to plug the bleed. During an operation it is desirable for a patient to lose as little blood as possible, so various devices have been developed in an attempt to provide bleeding-free cutting. For endoscopic procedures, it is also undesirable for a bleed to occur and not to be dealt with expediently, since the flow of blood may obscure the operator's vision. Instead of a sharp blade, it is known to use RF energy to cut biological tissue. The method of cutting using RF energy operates using the principle that as an electric current passes through a tissue matrix (aided by the ionic cell contents), the impedance to electron flow across the tissue generates heat. When a pure sine wave is applied to the tissue matrix, enough heat is generated within the cells to vaporize the water content of the tissue. There is thus a huge rise in the internal cell pressure that cannot be controlled by the cell membrane, resulting in rupture of the cell. When this occurs over a large area, it can be seen that the tissue is transected.

The above procedure works elegantly in lean tissue, but it is less efficient in fatty tissue because there are fewer ionic constituents to aid the passage of electrons. This means that the energy required to vaporize the contents of the cells is much greater, since the latent heat of vaporization of fat is much greater than the latent heat of vaporization of water. RF coagulation operates by applying a less efficient waveform to the tissue, whereby instead of being vaporized, the cell contents are heated to around 65° C., drying out the tissue by desiccation and denaturing the proteins in the vessel walls. This denaturing acts as a stimulus to the coagulation cascade, so clotting is enhanced. At the same time the collagen in the wall is denatured, turning from a rod-shaped to a coil-shaped molecule, causing the vessel to contract and reduce in size, giving the clot an anchor point, and a smaller area to be plugged.

However, RF coagulation is less efficient when fatty tissue is present because the electrical effect is diminished. It can thus be very difficult to seal fatty bleeders. Instead of having clean white margins, the tissue has a blackened burned appearance.

SUMMARY OF THE INVENTION

At its most general the present invention provides an electrosurgical cutting tool which comprises a pair of pivotable blades that are mechanically operable in a scissor-like or plier-like manner, and which have electrode structures capable of delivery RF energy and microwave energy to cut and/or coagulate tissue present in a gap between the blades. In particular, the invention relates to combined actuation and energy delivery mechanisms that are compact enough to enable the tool to be insertable through an instrument channel of a surgical scoping device, such as an endoscope, gastroscope or laparoscope. The device could also be used to perform open surgery, i.e. the bloodless resection of a liver lobe with the abdominal cavity open.

According to one aspect, the invention provides an electrosurgical cutting and coagulation tool having: a first blade and a second blade, joined at a pivot point, each blade comprising a planar body made of a first dielectric material separating a first conductive element on a first surface thereof from a second conductive element on a second surface thereof, the second surface facing in the opposite direction to the first surface; actuation means for causing relative rotation between the first and second blades about the pivot point to cause a gap between the first blade and second blade to change between an open position and a closed position, the relative rotation being substantially in the plane of the blades; a coaxial transmission line for delivering RF energy and microwave energy to the first blade and the second blade, the coaxial transmission line having an inner conductor and an outer conductor separated by a second dielectric material, wherein: the inner conductor and the outer conductor are each connected to one of the first conductive element and the second conductive element of the first blade; the inner conductor and the outer conductor are each connected to one of the first conductive element and the second conductive element of the second blade; the first conductive element and the second conductive element of each blade are able to act as active and return electrodes for sustaining an RF and microwave electric field therebetween, the RF and microwave electric field corresponding to RF energy delivered to the blades by the coaxial transmission line; and the first conductive element and the second conductive element of each blade are able also to act as an antenna structure for radiating a microwave electromagnetic (EM) field corresponding to microwave energy delivered to the blades by the coaxial transmission line. Although this aspect of the invention is capable of delivering RF and microwave energy, the invention may be used with only one of those types of energy.

The cutting tool is preferably configured to deliver RF energy and microwave energy both separately and in combination with each other (i.e. simultaneously). Accordingly, the cutting tool may be connected to receive energy from a microwave energy source and an RF energy source. A frequency diplexer/duplexer unit (or signal adder) may be provided for combining the RF and microwave signals. The frequency diplexer/duplexer unit may comprise a low pass filter to prevent the high frequency microwave energy from going back into the lower frequency RF energy source, and a high pass filter to prevent the lower frequency RF energy from going back into the higher frequency microwave energy source. The microwave energy source and RF energy source may be part of an electrosurgical generator, e.g. of the type disclosed in WO 2012/076844.

The electrosurgical cutting tool may be sized to fit inside the channel of an endoscope, laparoscope or the like. As such, it is preferable that the maximum diameter of the electrosurgical cutting tool (e.g. when in a closed position) is equal to or less than 10 mm, and more preferably equal to or less than 5 mm, and even more preferably equal or less than 3 mm. It is envisaged that a preferred embodiment will have a maximum diameter of 2.8 mm. The electrosurgical tool may include a protective sleeve (e.g. catheter or the like) which can surround the blades or even extend for the whole length of the instrument channel.

The structures of the first blade and the second blade may be substantially identical. Accordingly, the disclosure herein expressly contemplates that any feature described with reference to the first blade may also be present on the second blade.

However, in an alternative example, the blade structure defined above may be provided on only one of the blades. The other blade may comprise a passive structure, e.g. formed from a rigid dielectric material that does not affect the energy delivered from the opposing blade.

The first conductive element and second conductive element may be exposed on faces of the first blade and second blade that oppose each other across the gap. These faces may be referred to a "cutting edges" herein, since they correspond to the locations on the blades that are conventionally associated with mechanical cutting. The cutting edges may be arranged to perform mechanical cutting, which may be assisted by RF energy delivered from the first and/or second conductive elements (which may be referred to as electrodes). In one example, cutting is performed entirely mechanically (e.g. a "cold" cut), e.g. using sharpened edges on the blades. Microwave energy may be supplied to coagulate or ablate tissue before or after the mechanical cut is executed.

Each cutting edge may be a straight edge. The cutting edge of the blade is preferably perpendicular or substantially perpendicular to the plane of the planar body of the blade. The blades are preferably mounted on an axle about which they are free to rotate, each blade having a hole through which the axle passes. The blades are preferably mounted on the axle so that the inner surface of the hole and the outer surface of the axle lie flush against (i.e. in contact with) each other.

As discussed above, depending on the position of the pivot relative to the cutting edge of the blade, the first surfaces of the two blades may slide past each other (in a scissor-like manner), the cutting being caused in part by a shearing action as the first surfaces act as shearing surfaces and slide past each other. This scissor-like action occurs when the pivot point is located at a position which is removed from the cutting edge, in a direction perpendicular to the cutting edge. In this scissor-like configuration, the first surfaces of each blade are facing (and may be in contact with) each other when the blades are in the closed position, with the second surfaces of each blade facing away from each other, at the outside of the blades. In the closed position, the cutting edges of each blade have moved past each other and therefore face outwardly and in opposite directions from each other, i.e. the cutting edge of the first blade faces in an opposite or substantially opposite direction to the cutting edge of the second blade.

Alternatively, in a plier-like configuration, when the pivot point is located in line with the cutting edge, the cutting edges of the blades face each other and may contact each other when the blades are in the closed position. Accordingly, the cutting is caused in part as a result of the force between the two contacting cutting edges. In the present invention, it is preferable that the cutting of tissue is caused primarily by the RF energy, and not by the mechanical action of the shearing or force between the two blades. However, it is envisaged that the mechanical action will aid the cutting. Accordingly, for example, unlike household scissors or pliers, in the present invention, it is preferable that the cutting edge of the blade is flat, substantially flat or curved (e.g. rounded), rather than sharpened. In this way, it is ensured that the cut is effected primarily by the RF energy, rather than mechanical force, leading to a cleaner more carefully-controllable cut, which tends to result in less bleeding. This arrangement my also reduces the risk to the patient since there are no sharp blades or surfaces or edges introduced into the patient. In a closed position in this configuration, with the cutting edges touching or almost touching, the first surface of the first blade is adjacent to the second surface of the second blade and vice versa.

In embodiments of the present invention, it is preferred that as the blades are moved from an open to a closed position, that the electric fields associated with each blade are not unduly affected by the conductive elements on the opposite blade. Therefore, in the scissor-like configuration described above, it is preferable that, the inner conductor of the coaxial transmission line is connected to the first conductive element of the first blade, and to the second conductive element of the second blade. Likewise the outer conductor of the coaxial transmission line is preferably connected to the second conductive element of the first blade and the first conductive element of the second blade.

Conversely, in a plier-like configuration, as the blades are moved towards each other (rather than across each other) the first conductive element on the first blade moves to be adjacent to the second conductive element on the second blade, and vice versa. Therefore, in this configuration it is preferable that the inner conductor of the coaxial transmission line is connected to the first conductive element of the first blade, and to the first conductive element of the second blade. Likewise the outer conductor of the coaxial transmission line is preferably connected to the second conductive element of the first blade and the second conductive element of the second blade.

Even though the opposing surfaces receive electrical signals having opposite polarities, there is little risk of short-circuiting when the blades move together, because in use, there will always be biological tissue separating the two blades. To further ensure this, one or both of the blades may include a spacing means which prevents the cutting edges of each blade from coming into contact when the blades are closed. The spacing means may be located on one or both of the blades ensuring that there is always a sufficient degree of spacing between the cutting edges of the blades, even in the closed position. The spacing means may comprise a projection on one or both of the blades. When the two opposing fields from opposite blades are in close proximity, the cutting or coagulation capability of the device could be enhanced, since the distance between the blades may be small enough to create electric fields between the blades that have a similar magnitude to those produced by the conductive elements on each individual blade. In this arrangement, the mechanism of energy delivery into tissue is similar to that of conventional RF bipolar devices, but may be more efficient.

On each blade, the first and second conductive elements may be in the form of one or more layers of metallization formed on the opposite surfaces of the first dielectric material. More specifically, the first and second conductive elements may be arranged to set up a local electric field at a contact region in which the instrument tip or edge makes contact with the biological tissue. The local electric field can be extremely high, which may cause a microplasma (i.e. a hot thermal plasma) to be formed at the cutting edge, where contact with the biological tissue is best desired. This microplasma may be particularly efficient in terms of achieving efficient cutting. To resist any adverse effects caused by the high temperature microplasma, the first and second conductive elements may include portions e.g. plated regions at and adjacent to the cutting edge, which are made from conductive material having a high melting point, e.g. 1500° C., such as titanium, tungsten and the like. Using such materials helps to ensure that the first and second conductive elements are not eroded by the microplasma which is generated.

The first and second conductive elements may also include connecting portions made from conductive materials having lower melting points such as silver, gold and the like, which are deposited or plated on the higher melting point conductors. The connecting portions may facilitate connection of the inner and outer conductors of the coaxial transmission line e.g. by soldering or the like. In one embodiment, a titanium tungsten (TiW) seed layer may be used with a layer of silver or gold deposited on top. The lower melting point material may be deposited on the higher melting point material only in the region where the coaxial transmission line inner and outer conductors are to be attached, i.e. at a proximal end of the blade only, and spaced from the cutting edge (where the microplasma will form) e.g. surrounding the hole through which the blade may be mounted on an axle. This arrangement follows from the fact that the electric field at the point where the coaxial transmission line connects to the blades should be relatively low and so the temperature at this point should be much lower than the melting point of the lower melting point material. The layers of metallization are preferably made from biocompatible materials such as gold, silver and titanium.

RF tissue cutting may be produced at the cutting edge if the first dielectric material has a dielectric constant greater than that of air, and the thickness of the first dielectric material at the cutting edge is small, preferably 1 mm or less, for example 0.5 mm. This ensures that the current is allowed to flow smoothly along the preferential return path. It also produces a high enough electric field to produce the microplasma.

As discussed, the blade is also arranged to receive microwave frequency energy from the coaxial transmission line. The coaxial transmission line may therefore be arranged to convey a microwave frequency signal separately from or simultaneously with the RF signal. Hence the first and second conductive element are arranged on the first dielectric material to act as a near field antenna or electrode to radiate microwave EM radiation corresponding to the received microwave signal. The different treatments of microwave and RF signals is possible as a result of the blade being "seen" differently by the different frequency signals. For the RF signal, the blade may be modelled like a parallel plate capacitor. The electric field set up by the RF signal between the first and second conductive elements can be substantially contained within the first dielectric material, by setting back the edges of the first and second conductive elements from e.g. the outer edges of the first dielectric material. To perform cutting using the RF energy, it is clearly desirable for the field to extend out of the first dielectric material. This may be achieved by extending the edges of the first and second conductive elements to (but not across) the cutting edge of the blade, in a region designated the RF cutting portion. Then, the RF field which is set up between the two plates of the parallel plate capacitor (i.e. the first and second conductive elements separated by the first dielectric material), and coupled into the biological tissue, through making contact with one or more edges of the blade, may create a controlled microplasma and the microplasma may enable or enhance the RF tissue cutting process. The edge not involved in the scissor action, i.e. opposite the cutting edge, is preferably de-activated or arranged such that it will not deliver RF or microwave energy into contact tissue— this may be achieved by cutting back the metallisation around the on the edges that are not involved with the scissor action.

Meanwhile, for the microwave signal, the blade may be modelled as a parallel plate transmission line or planar transmission line, e.g. having a physical length equal to a multiple of half an electrical wavelength of the microwave energy. The radiation pattern of the microwave frequency EM energy in this case depends on the overall shape of the blade, and the microwave feed structure, i.e. the coaxial transmission line. In this case, the gap at the proximal end between the coaxial transmission line and the first conductive element plays an important role in ensuring that the microwave energy from the source is matched in terms of impedance with the load impedance presented by the tissue. The overall length of the planar transmission line arrangement is also important in terms of matching the impedance (or energy delivery) of (or from) the coaxial transmission line with (or into) the biological tissue, i.e. the structure may form a quarter wave impedance transformer, or a half wavelength resonator. Using known simulation tools, the geometry may be adjusted to control from which edges the microwave frequency energy EM energy is radiated. The preferred simulation is CST Microwave Studio.

The opening and closing of the blades may be effected in numerous ways. In particular, it is preferable that at least part of the actuation means is movable relative to the pivot point. More specifically, it is preferable that at least part of the actuation means is movable relative to the pivot point in a direction which is parallel or substantially parallel to a longitudinal axis of the coaxial transmission line. The actuation means preferably includes one or more push rods arranged to contact part of the blades, the push rods controllable from a position which is substantially proximally removed from the blades themselves. In this way, the opening and closing of the blades may be effected by a user when the distal end of the cutting tool is in use inside a patient.

The inner conductor of the coaxial transmission line may be hollow, i.e. to define a channel running therethrough. The channel may be used to convey material to or from the instrument, e.g. to provide or remove fluid from the treatment site or to convey part of the actuation means, e.g. a push wire or control rod. It may also contain an image sensor and illumination to help locate the tissue to be resected or cut/coagulated—this is of particular interest for endoscopic or laparoscopic applications—in this particular instance, the scissor device may also perform the function of an endoscope, gastroscope or laparoscope. The actuation means may further include one or more control wires arranged to steer the instrument.

The actuation means may comprise an actuation element that is movable relative to the pivot point. For example, the actuation element may include a push rod that is operably connected to the first blade and/or the second blade. The actuation element may be slidably connected to the coaxial transmission line to ensure that its longitudinal movement path is well defined along, e.g. if it extends through the instrument channel of a surgical scoping device.

In one example, the actuation means may comprise a cam arrangement arranged to effect relative rotation of the blades. Here, a "cam arrangement" refers to an arrangement whereby linear motion of a component is converted into rotary motion of the first and/or second blade as a result of the component sliding against a given part of the blade.

The cam arrangement may comprise: a push rod mounted to slide longitudinally with respect to the pivot point, and a guide path formed on the first blade, wherein the push rod is operably engaged with the guide path, and wherein the guide path is offset from the longitudinal direction, whereby longitudinal movement of the push rod relative to the pivot point causes the first blade to pivot with respect to the pivot point. The guide path may be a linear track extending in a direction that is offset from the pivot point, e.g. angled relative to the longitudinal direction. The push rod may be constrained so that it can move only in the longitudinal direction, and may comprise a follower mounted in and constrained to lie on the linear track. In order for the intersection between the follower and guide path to remain in line with the longitudinal direction of the push rod, the guide path must change orientation as the follower moves.

The cam arrangement may be applied on both blades, or may be applied on one blade only, in which case the blades may be hinged in a manner that ensures they move symmetrically about the pivot point.

The guide path may be in the form of a recess in the surface of the blade, or alternatively in the form of a hole or slot through the blade, and the follower may be in the form of a projection at a distal end of each of the push rods. Reciprocating motion of the push rod, i.e. forwards and backwards motion which is substantially linear, causes the point of contact of the projection and the guide path to change, and the guide paths are preferably be shaped such that the change in contact point as the projection slides along the guide path causes rotation of the blade about the (fixed) pivot point. For example, the guide path may be substantially linear, and oriented obliquely relative to the forwards/backwards direction of motion of the push rod. Naturally, in order for the blades to rotate in opposite directions about the pivot point, the guide path on one blade may be slanted in the opposite sense to the guide path on the other blade. By connecting the blades in this way, a high level of control is possible, and the number of moving parts is reduced. In an alternative embodiment also employing a cam arrangement, the guide path may be in the form of a raised region on the surface of the blade, and the push rod may have a corresponding recess at its distal end. In this case, the principle of operation remains unchanged from the slot/projection arrangement.

In the above embodiment, the push rods are preferably located on the end of a hollow tube structure or jacket which surrounds the coaxial transmission line, the inner surface of which is preferably flush with an outer surface of the coaxial transmission line. In a preferred embodiment, the tube is fixed in position with respect to the coaxial transmission line, and the push rods are able to move back and forth within the channels of the tube in which they are located in. Alternatively, the tube may be made of a material which allows it to slide back and forth along the outer surface of the coaxial transmission line with ease, to achieve actuation by moving the tube, rather than moving the push rods within the tube.

The two push rods preferably extend from a distal end surface of the tube. Because the blades, and more importantly the pivot point are connected rigidly or substantially rigidly to the coaxial transmission line, motion of the tube and push rods relative to the coaxial transmission line and pivot point is able to actuate the opening and closing of the blades as discussed. By using a tubular structure, which slides along the outer surface of the coaxial transmission line or in which the push rods themselves slide, the direction of motion of the push rods is constrained to be parallel or substantially parallel to the longitudinal axis of the coaxial transmission line at its distal end, allowing improved control. Having a tube structure with a push rod for each blade as described here presents an improvement over e.g. a single push rod which is coiled around the coaxial transmission line. Such a structure, when the device is contained within a catheter, tends to push to the outer edges of the catheter, and subsequently gives rise to an inconsistent relationship between the sliding motion and the degree to which the blades are open. Such imprecision is undesirable in e.g. delicate surgical resection procedures.

In some cases, depending for example on the angle of the guide path relative to the direction of motion of the push rods and the stiffness of the pivot point between the two blades, as the projection (or recess) of the push rod moves back and forth in the guide path, it may experience a resistive force from the edges of the guide path tending to splay the two push rods apart, rather than to open the blades. In order to prevent such splaying, which may lead to weakening or breakage of the push rods, they may be connected using a bracing structure.

Depending on the specific dimensions of the cam arrangement as described above, movement of 3.5 mm of the push rods may translate into an opening of 7 mm when the blades are in the fully opened position. In situations where this separation or level of control is insufficient, a geared handle may be affixed to the proximal end of the tube structure. This prevents the need to use longer blades, which can lead to problems when the tool must be inserted into a patient by means of an endoscope.

In alternative arrangement, which may also make use of the tube structure having two push rods, the rods may be made of a wire (or similar) which is rigidly connected to the blade at the pivot. The wire is preferably shaped, e.g. bent, so that back and forth motion of the wire rotates the blade about the pivot, for example like a door handle. The wire is preferably pre-shaped into a curved shape, and preferably the portion of the wire contacting the blade is the part having the greatest angular displacement relative to the direction of the back and forth motion of the push rods. In a preferred embodiment, the wire is made of nitinol. This arrangement is advantageous that it is simpler to manufacture than the cam arrangement.

In another example, the actuation means may comprise a linkage having a proximal end pivotably connected to the push rod and a distal end pivotably connected to the first blade at a location offset from the pivot point. Each blade may have an arm extending from its proximal end to provide the location for connecting to the linkage. The arm may be connected to the distal end of a push rod via the linkage. The linkage is preferably in the form of a substantially linear piece of rigid material which is pivotally connected to the push rod at its proximal end and the arm of the blade at its distal end. In this arrangement, because the linkage establishes a fixed distance between the end of the push rod and the arm of the blade, relative motion between the pivot point and the push rod causes the angle between the arm of the blade and the linkage to increase/decrease (depending on the direction of motion of the push rod), and so is able to cause opening/closing of the blades. Preferably, each blade is connected to a different linkage, the two linkages both being connected pivotably to the distal end of the push rod at the same point. In this way, a symmetrical arrangement of the two blades is achieved, helps to ensure that the push rod is only able to move in a forward-backward direction, without straying sideways. This linkage arrangement is a robust arrangement, with reduced risk of bending or breaking of the push rod or other components. In order to work well, the push rod in the linkage arrangement must be located centrally, rather than peripherally. This may be achieved by having a hollow inner conductor of the coaxial transmission line, having a channel running therethrough. In this case, if a metal push rod is used, e.g. a nitinol wire or the like, it may be electrically insulated from the inner surface of the channel. This may be done using either an insulating coating on the inner surface of the channel, or the outer surface of the push rod, or both.

In another example, the push rod may comprise a wire having a preformed curved distal portion that is rigidly secured to the first blade.

The tool may comprise a biasing means arranged to urge the first blade and the second blade towards the open position. The biasing means may be a spring (e.g. a coil spring or a leaf spring) present between the blades. The biasing means is preferably arranged to maintain the blades in an open position.

The actuation means may include a collar that is slidably mounted with respect to the first blade and second blade, the collar being movable between a first position in which it encloses the blades to hold them in the closed position, and a second position in which the blade are exposed to permit them to be opened. The collar preferably has a diameter which is greater than the maximum width of the blades when in a closed position. In a first positon the collar may enclose the blades, to hold them in a closed, or partially closed position, thus reducing the risk of injury to a patient. Then, as the collar is moved backwards into a second position, as more of the blades are exposed, they are allowed to open to a greater degree, as the contact point between the outer edge of the blade and the lip of the collar changes. More specifically, in the second position, part of the blades which was enclosed in the first position becomes exposed, the exposure allowing the blades to open to a greater degree. Like the embodiment employing a wire to actuate opening and closing of the blades, this embodiment also has a simpler structure than the cam and linkage mechanisms, with fewer moving parts, and fewer guide wires/push rods.

The blades may be mounted in a clevis structure which is located at the distal end of the cutting tool, the clevis structure comprising a base for attached to the coaxial transmission line, and a housing that defines a longitudinal recess for receive the first blade and second blade.

The clevis structure may be a piece of material such as stainless steel with a central recess, to give it a substantially U-shaped side profile. In a preferred embodiment the blades are pivoted around an axle which extends from one side of the recess to the other, the axle preferably located towards the distal end of the clevis structure, so that as much of the blade as possible may be exposed to the surrounding biological tissue. The axle may be sealed in place with a pin at each end. The width of the recess in a direction perpendicular to the planes of the blades is preferably approximately the same as the total thickness of the two blades contained therebetween. In this way, the inner walls of the recess provide additional support for the blades, and ensure that in use they are constrained only to move in a plane, rather than wobbling in a direction which is perpendicular to that plane. The floor at the base of the recess should have a large enough area that both the inner and outer conductor of the coaxial cable may be exposed, in order that they may form connections with the first and second conductive elements of each blade. The recess floor is preferably substantially flat, though it may be curved. The clevis structure is preferably cylindrical, in order to form a continuous surface, with no sharp edges, with the outer surface of the coaxial transmission line. The clevis structure may further include a hemispherical or other curved portion at its distal end, also to remove sharp edges which may cause injury to a patient when the cutting tool is in use.

In embodiments of the invention including one or more push rods, e.g. when the actuation means includes a cam, the inner walls of the recess of the clevis structure preferably include one or more guides, e.g. grooves which support the push rods during back-and-forth motion. This helps to prevent bending or splaying apart of the push rods.

The electrical connections between the inner conductor and outer conductor of the coaxial transmission line and the first conductive element and second conductive element on each of the first blade and the second blade may be made via the axle, which is the point of least movement when the blades are rotating relative to each other. Accordingly, when the blades are mounted on an axle, the connection between the inner/outer conductor and the conductive elements on the surface of each blade are preferably made via conducting structures located on an outer surface of the axle. Correspondingly, the inner surface of the hole of each blade may include a conductive coating which is electrically connected to the conductive element on the corresponding surface of that blade. In a preferred embodiment, the first conductive element on the first surface of the blade may extend onto the inner surface of the hole (through which the axle passes) of the blade. Similarly the second conductive element on the second surface of the blade may also extend onto the inner surface of the hole. In order to prevent a short circuit, the metallization from the first surface and the metallization from the second surface which extend onto the inner surface of the hole must be electrically isolated from each other. This is most easily achieved by having a space therebetween, and the axle being made from an insulating material. In order to connect to the conductors of the coaxial transmission line, the inner conductor may extend axially into the space between the two blades, and contact a conductive sleeve, coating or strip on the outer surface of the axle. The conductive coating extends into the portion of the axle which is in contact with the metallization on the inner surface of the hole of the first blade to establish an electrical connection between the inner conductor and the metallization on the first surface of the blade. Similarly, the outer conductor, or a length of conductive material which is connected to the outer conductor, may extend axially, and contact a conductive coating or strip on the portion of the axle which is in contact with the inner surface of the hole of the first blade, to establish an electrical connection between the outer conductor and the metallization on the second surface of the blade.

The same applies for the second blade, except the outer conductor and the inner conductor, or strips of conducting material which are connected to each must cross paths, in order that the outer conductor is in electrical contact with the first surface of the second blade, and the inner conductor is in electrical contact with the second surface of the second blade. This is best achieved by having strips of conducting material extending from the distal ends of each conductor, which are able to cross each other without contacting each other due to the three dimensional nature of the device. In some embodiments, strips of conducting material extending from either or both of the inner conductor and the outer conductor of the transmission line may be located on the inner walls of the clevis structure in order to ensure that they do not get bent or broken in use.

In an alternative embodiment, the point of electrical contact may not be on the pivot, but may be on the first/second surface of the blade itself. By their very nature, during rotation of the blades about the pivot, these parts will move a greater distance than the inner surface of the hole on each blade. Accordingly, in some embodiments, the shape of the metallization on each surface of each blade must be selected to ensure that contact is maintained with the inner/outer conductor of the coaxial transmission line at all times during motion of the blade, in order to maintain uniform contact while the cutting tool is in use.

In other embodiments, wherein the inner conductor is connected to the first surface of each blade, and the outer conductor is connected to the second surface of each blade, similar, but simpler structures are envisaged, wherein the strips of conducting material do not need to cross each other in anyway. For example, the inner conductor may just branch into two and extend between the two blades, electrically connecting with them either via a conducting sleeve on the axle or connecting directly with the blade. Similarly, a conducting strip may extend from each side of the end surface of the outer conductor, each conducting strip extending into the gap between the clevis wall and the second surface of the blade (which is on the outside), and forming an electrical contact either with the conducting element on the blades' surfaces or via a conducting sleeve on the axle. This configuration may be employed for example in the plier-like configuration where the cutting edges may meet face-on when the blades are in the closed position.

As an alternative to delivering RF and/or microwave signals from both of the blades simultaneously, in some embodiments of the present invention, the signals may be alternated between the blades. This may be achieved by having a separate input into each of the blades. Thus, according to a second aspect of the invention, there is provided an electrosurgical cutting tool having: a first blade and a second blade joined at a pivot point, each blade comprising a planar body made of a first dielectric material separating a first conductive element on a first surface from a second conductive element on a second surface, the second surface facing in the opposite direction to the first surface; actuation means for causing relative rotation between the first and second blades about the pivot point, between and open position and a closed position, the relative rotation being substantially in the plane of the blades; a first coaxial transmission line having a first inner conductor and a first outer conductor separated by a second dielectric material, the first coaxial transmission line arranged to deliver RF and microwave frequency signals for the first blade, wherein the first inner conductor and the first outer conductor are respectively connected to the first conductive element and the second conductive element of the first blade, a second coaxial transmission line having a second inner conductor and a second outer conductor separated by a third dielectric material, the second coaxial transmission line arranged to deliver RF and microwave frequency signals to the second blade, wherein the second inner conductor and the second outer conductor are respectively connected to the first conductive element and the second conductive element of the second blade, and wherein: the first conductive element and the second conductive element of each blade are able to act as active and return electrodes for sustaining an RF electric field therebetween, the RF electric field corresponding to the RF signal delivered to the first and second blades by the first and second coaxial transmission lines respectively, and the first conductive element and the second conductive element are able also to act as an antenna structure for radiating a microwave frequency EM field corresponding to the microwave signal delivered to the first blade and the second blade by the first and second coaxial transmission lines respectively.

Where compatible, the optional features presented above also apply to the second aspect of the present invention. In particular, this arrangement is compatible with all of the blade structures set out above, and all of the actuation mechanisms may be used with this structure. The clevis structure (and the corresponding related optional features) are also fully compatible with embodiments of the second aspect of the present invention. The electrical connections between the conductors of the coaxial transmission lines are further simplified relative to the electrosurgical cutting tool of the first aspect of the invention because there is no need to cross the conducting strips. The connections may still be made via conducting sleeves on the axle, or by direct contact with the conductive elements on the surface of the blades. In embodiments where the connection is made via conducting coatings, sleeves or strips on the axle, said coatings, sleeves, or strips which are connected to different blades are preferably electrically isolated from each other in order to ensure that signals which are supplied to the first blade do not reach the second blade and vice versa, i.e. to ensure that only one blade is active at a given time.

The first and second coaxial transmission lines are preferably contained in a catheter or the like, and are preferably attached to the sides of the catheter. The actuation means may be in the form of the cam arrangement, wherein a jacket or similar tube structure containing push rods as described above is located on the outer surface of the catheter. The jacket or tube structure may also be located on an inner surface of the catheter. Alternatively, a central push rod may be located inside the gap or channel between the first and second coaxial transmission lines, as in the case of the linkage arrangement as described above.

In order to alternate microwave and/or RF signal delivery between the first and second blades, the tool may further include alternation means configured to alternate delivery or microwave/RF signals between the first and second blade. The alternation means is preferably in the form of an alternating coaxial switch, for example a single-pole double-throw switch, which is connected between an output of a microwave and/or signal generator, and the ends of the coaxial transmission lines, wherein the pole configured to alternate rapidly between the two throws, one connected to each of the coaxial transmission lines. By alternating the energy delivery between the two blades, it is possible to use standard 50Ω transmission lines without the need for impedance transformers. There are also advantages related to voltage breakdown, since the maximum voltage should be halved. In a preferred embodiment, the alternating coaxial switch may operate at 50 Hz, i.e. have a cycle of 20 ms.

In another aspect, the present invention provides an electrosurgical apparatus including: an electrosurgical generator arranged to output RF energy and microwave energy; and an electrosurgical cutting tool as set out above (i.e. according to either the first or second aspect described herein) connected to receive RF energy and microwave energy from the electrosurgical generator. The apparatus may include a signal alternator arranged to alternately switch RF energy or microwave energy from the electrosurgical generator between the first blade and the second blade.

The signal alternator may function to switch the microwave and/or RF energy between the two blades. This can permit more power to be delivered at the distal end of the device, whilst avoiding a risk of the blades shorting out. The signal alternator may be a switch element, e.g. comprises any one of a co-axial switch, PIN diode, and varactor diode power switch. The switch may be contained in the handpiece, or may be located at the distal end where the blades are located.

It may be desirable to switch the energy delivered to the first and second blade in less then 1 second or even less than 100 ms, in order for the energy delivery to appear to quasi-continuous. In one example, a 150 ms burst of energy may be delivered from a first blade, followed by a 100 ms, after which a 150 ms burst is delivered from the second blade. In this arrangement, it is possible to still gain advantage from having the two separate blades that can deliver RF and microwave energy.

Throughout the present application, RF may mean a stable fixed frequency in the range from 10 kHz to 300 MHz, and microwave frequency may mean a stable fixed frequency in the range of 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz and 24 GHz.

Furthermore, throughout the present application, when the terms "conductor", "conductive", "conducting" and the like are used, this should be understood to mean electrically conducting unless clearly stated otherwise.

BRIEF DESCRIPTION OF THE DRAWINGS

Embodiments of the invention are discussed in detail with reference to the accompanying drawings, in which.

DETAILED DESCRIPTION OF THE DRAWINGS

Figure 1:
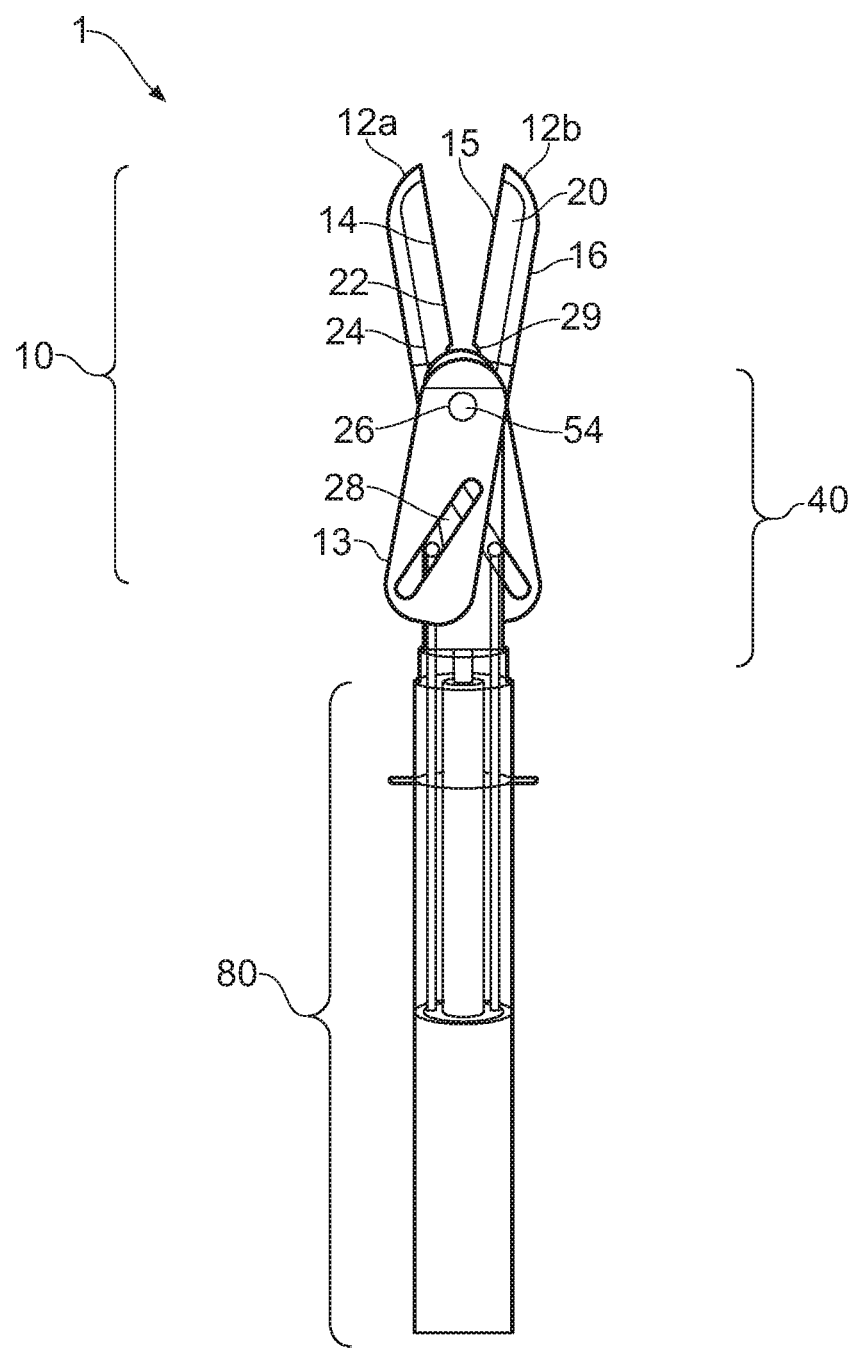
FIG. 1 shows a cutting tool according to an embodiment of a first aspect of the present invention.

FIGS. 1 to 4E show several views of a cutting tool 1 according to an embodiment of the present invention. The cutting tool 1 may broadly be divided into four sections: blade arrangement 10, clevis structure 40, actuation mechanism 60 and coaxial transmission line 80. These parts will be described in turn with reference to the relevant drawings. The same reference numerals are used in all of FIGS. 1 to 4E, for the same features.

FIG. 1 shows a perspective view of a cutting tool 1 including all four sections described above. Blade arrangement 10 is made up of a first blade 12a and a second blade 12b. The blades 12a, 12b are substantially identical, and are mounted onto the cutting tool 1 facing in opposite directions. Since the blades are substantially identical, features are only labelled in respect of one blade, or the other, apart from where it is useful to differentiate between the two blades. In this case, reference numerals for features of the first blade are denoted "a" and reference numerals for features on the second blade are denoted "b". In the following description, these are omitted since the structural features of each blade are the same.

The blade 12 consists of two main parts, a pivot part 13 and a blade part 15. As can be seen in FIGS. 4A to 4E, the blade part 15 is set back from (i.e. is located proximal to) the pivot part 13. This is described in more detail later.

The blade part 15 of each blade 12 is a planar ceramic body having a straight cutting edge 14 defining a front of the blade 12 and a curved back edge 16 opposite to the cutting edge. The cutting edge 14 defines a flat cutting surface. A first electrode in the form of a metallization layer 20 is present on the top surface 21 of the blade. A similar metallization layer is also present on the bottom surface of the blade, to form a second electrode (not shown in the drawings). The metallization 20 has a similar shape to the blade part 15 itself. The front edge 22 of the metallization 20 extends all the way to the cutting edge 14 of the blade part 15, but does not extend down onto the cutting surface. The back edge 24 of the metallization 20 is curved and runs generally parallel to the back edge 16 of the blade part 15. The back edge 24 of the metallization is spaced from the back edge 16 of the blade part 15 so that when the cutting tool 1 is in use, no or a negligible electric field appears at the back surface, where cutting/coagulation is not desired.

Similarly, the front edge 22 of the metallization 20 does extend to the cutting edge 14 of the blade part 15 so that a high-energy RF electric field may be generated between the first and second electrodes on the blade 2, across the cutting surface.

Pivot part 13 is a substantially rectangular planar body, having curved corners, which is attached at a proximal end 17 of blade part 15. A hole 26 runs through the pivot part 13, for receiving an axle 54 about which the blade 2 is free to rotate. The pivot part 13 also includes an elongate slot 28, which is oriented obliquely with respect to the cutting edge 14. The purpose of the slot 28 is described in more detail below, during discussion of the operation of the cutting tool 1. A notch 29 is also present in the region between the pivot part 13 and the blade part 15.

The blade part 15 is set back from the pivot part 13, in the plane of the page, when looking at e.g. FIG. 1.

In this way, the first blade 12a and the second blade 12b may be mounted on the cutting tool 1, so that when they are rotated into a closed position (i.e. the position shown in FIG. 4E), the cutting edges meet each other face on, as do the edges on a pair of pliers, rather than sliding past each other, as would the edges of a pair of scissors.

Figure 2A:
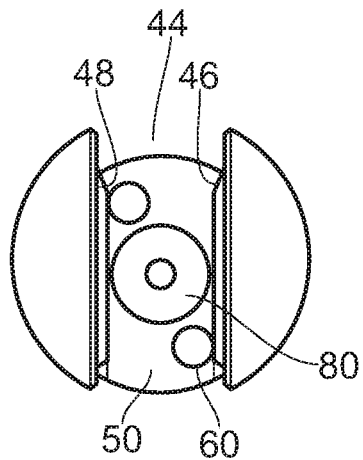
FIGS. 2A to 2C show top and side views of a clevis structure, and distal end of a coaxial cable, which may be used in embodiments of the present invention.
Figure 2B:
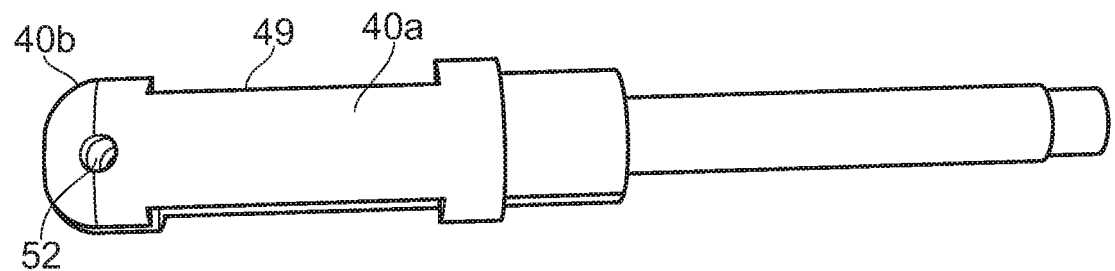
Figure 2C:
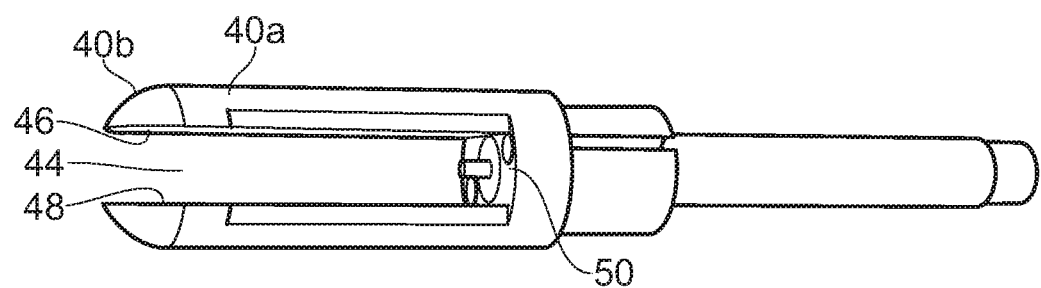
Figure 3A:
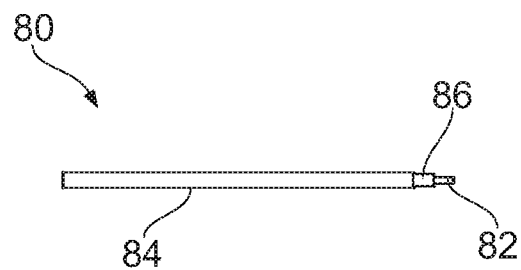
FIGS. 3A to 3E show a cutting tool according to an embodiment of the present invention, with various layers cut-away, in order to show the internal actuation mechanism of that embodiment.
Figure 3B:
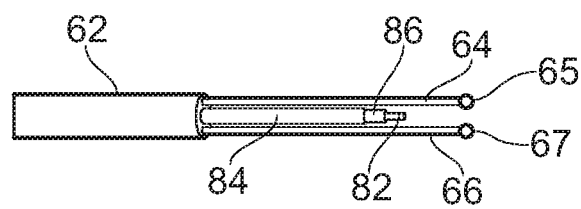
Figure 3C:
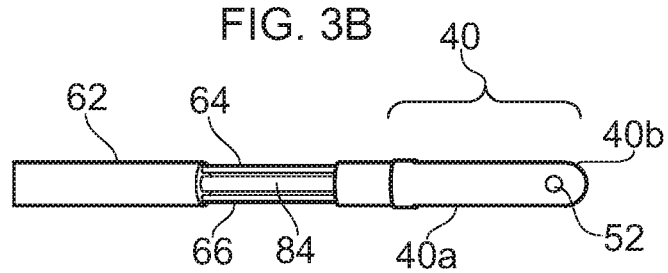
Figure 3D:
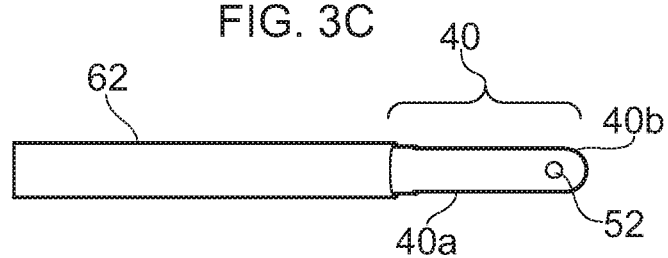
Figure 3E:
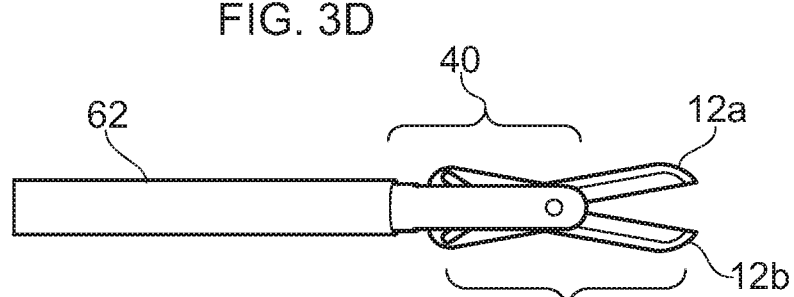

FIGS. 2A to 2C show the clevis structure 40, on which the blades are mounted, in more detail. Clevis structure 40 is formed of a cylinder 40a of e.g. stainless steel, having a domed distal end 40b. A recess 44 having a rectangular cross-section (see FIG. 2C in particular) runs almost the full length of the clevis structure 40, defining two elongate walls 46, 48, each wall defining an inner surface inside the recess 44. The recess also has a base 50, joining the inner surfaces 47, 49. In FIG. 2A, end surfaces of the actuation mechanism 60 and the coaxial transmission line 80 can be seen. Towards the distal end 42 of the clevis structure 40, a hole 52 is present in each of the walls 46, 48. In the present embodiment, the hole is located at the boundary between the cylindrical and domed portions of the clevis structure 40 in order to accommodate the full length of the pivot part 13 within the recess 44. An axle 54 may be passed through each of the holes 52, onto which the blades 12 may be mounted through hole 26. The blades are not shown in FIGS. 2A to 2C in order to better show the structure of the clevis structure 40 itself. As best shown in FIG. 2B, a rectangular notch 49 is present at the outer edges of each of the walls 46, 48. The coaxial transmission line 80 is exposed at the base 50 of the clevis structure 40. The coaxial transmission line, including the inner conductor 82, outer conductor 84 and dielectric material 86 which separates the two is shown better in e.g. FIGS. 3A and 3B.

FIGS. 3A, 3B and 4A to 4E shows the actuation mechanism 60, which is used to open and close the blades 12a, 12b in the cutting tool 1 of this embodiment of the invention, in particular FIGS. 4A to 4D show the mechanism with the clevis structure 40 omitted, to show the various stages of actuation. The actuation of the blades 12a, 12b is effected by a cam arrangement which is made up of projections at the end of push rods, which interact with the slots 28a, 28b in each blade 2. More specifically, a jacket 62 is located around the outer surface of the coaxial transmission line 80. The jacket contains two grooves, each containing a rigid push rod 64, 66. The push rods 64, 66 are movable back and forth relative to the jacket 62, in the direction of the longitudinal axis of the jacket. Accordingly, the length to which they protrude from the end surface 63 of the jacket may be varied. At the end of each push rod 64, 66 is a projection 65, 67. Each of the projections is arranged to rest in the slot 28 of one of the blades 12, when the blades are mounted on the axle 54.

Figure 4A:
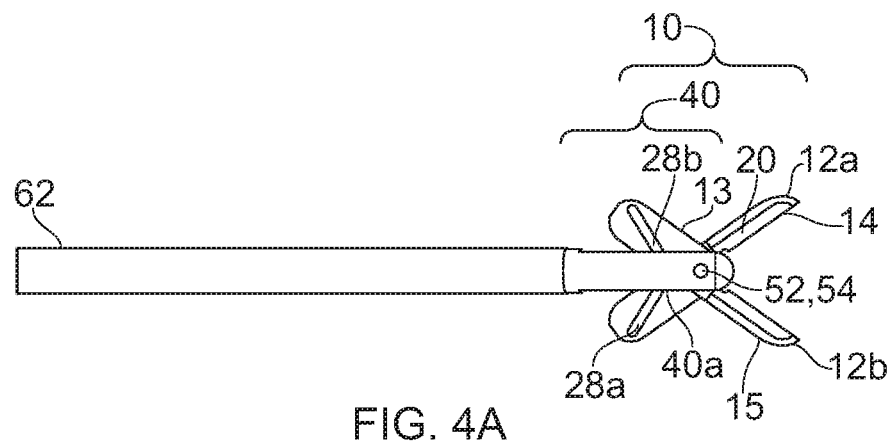
FIGS. 4A to 4E show a cutting tool according to an embodiment of the present invention at successive stages of the blades' moving from an open to a closed configuration.
Figure 4B:
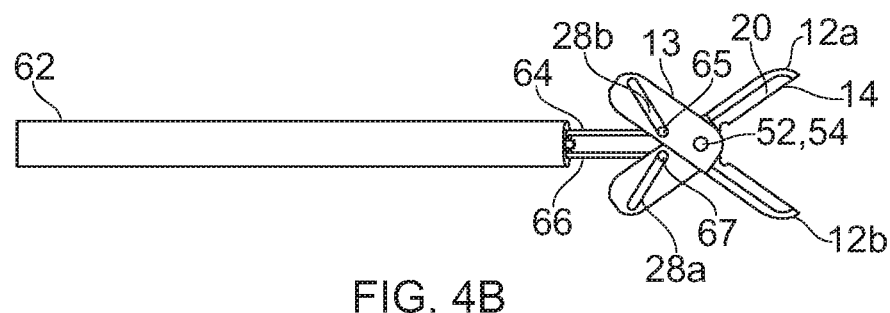
Figure 4C:
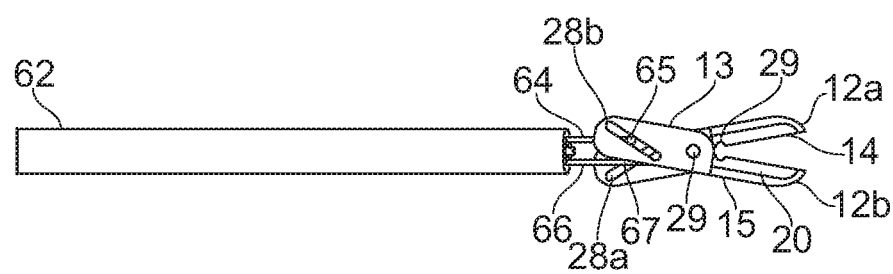
Figure 4D:
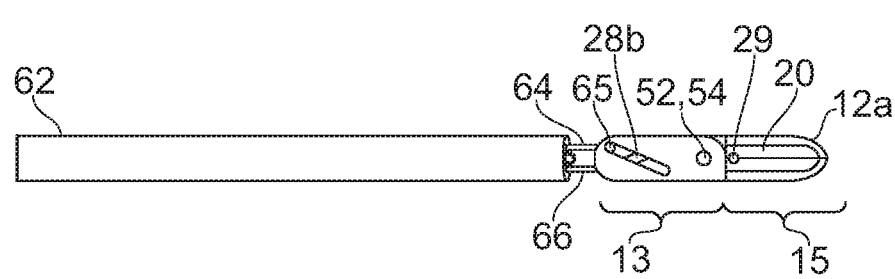
Figure 4E:
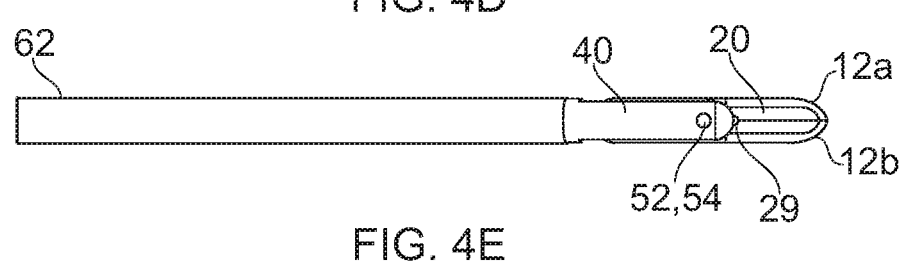

The opening operation of the actuation mechanism 60 will now be described with reference to FIGS. 4A to 4E. In a fully closed state, as shown in FIG. 4E, the push rods 64, 66 are retracted to the greatest extent possible.

They are unable to retract further due to the contact between the cutting surfaces of the blades 12a, 12b. The actuation mechanism 60 of the present embodiment relies on relative motion between the pivot point 25 and the projections 65, 67. In order to achieve this, it is necessary that the location of the pivot point 25 is therefore fixed with respect to the end surface 63 of the jacket 62, from which the push rods 64, 66 protrude. In use, the pivot point 25 is kept stationary and the push rods 64, 66 moved back and forth, in order to keep translational motion of the blades 12 to a minimum.

To open the blades 12, the push rods 64, 66 are moved forward, to protrude more from the end surface 63 of the jacket 62. The push rods 64, 66 are rigid and constrained to move in the longitudinal direction of the jacket 62. The slots 28a, 28b and at a non-zero angle relative to the longitudinal direction, which means that the longitudinal movement of the projections 65, 67 forces the blades to pivot about the pivot point 25 as the projections 65, 67 bear against the walls of their respective slots. When the projection reaches the distal end of the slot 28a, 28b, the push rods 64, 66 can protrude no further from the end surface 63 of the jacket 62, and so the blades 12 are maximally open, as shown in FIG. 4A. In order to close the blades 12 again, the push rods 64, 66 are retracted. When the blades 12 are closed, as in FIGS. 4D and 4E, the push rods 64, 66 can be retracted no further since the blades 12 cannot rotate any further, and the projections 65, 67 are located at the end of their respective slots 28a, 28b.

Figure 5A:
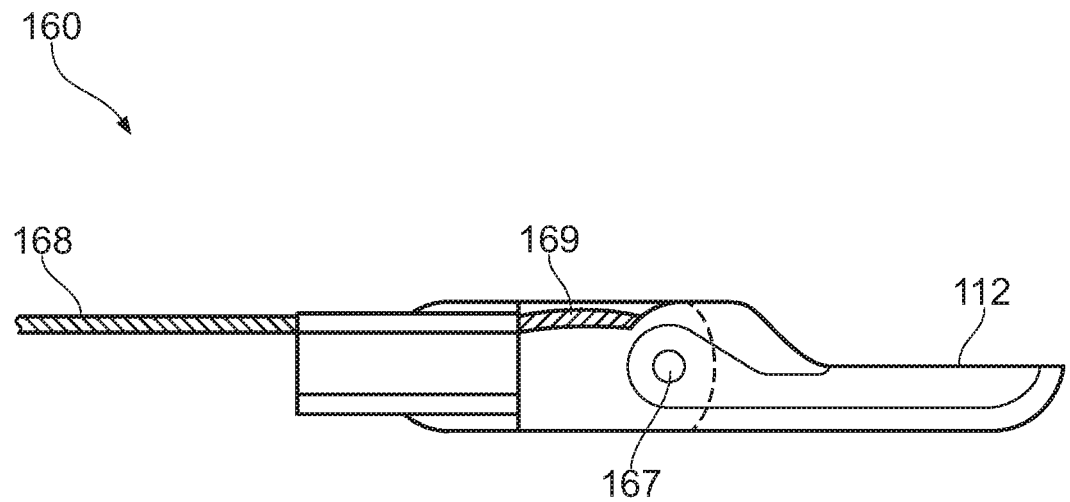
FIGS. 5A and 5B show an actuation mechanism which may be used in embodiments of the present invention.
Figure 5B:
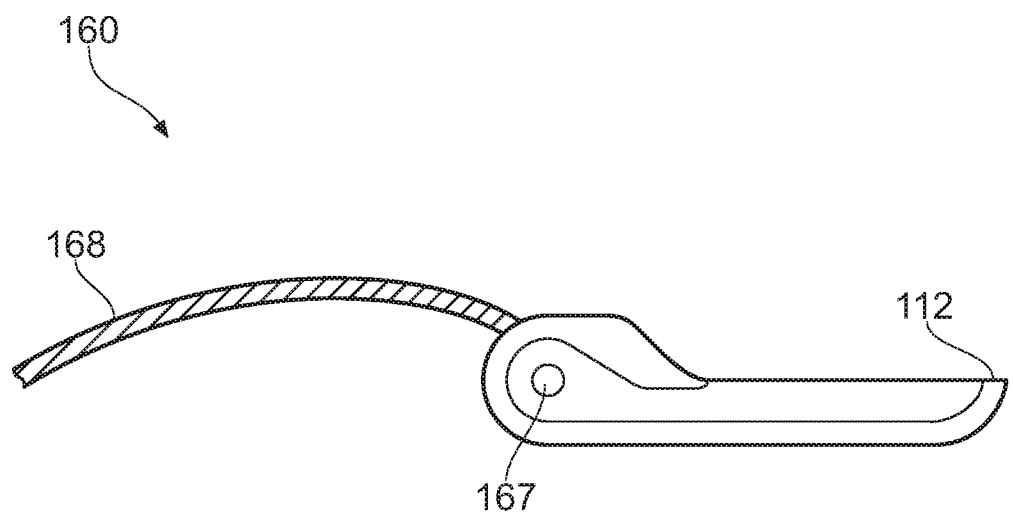

An alternative actuation mechanism 160 is shown in FIGS. 5A and 5B. In this arrangement a curved nitinol wire 168 is rigidly attached to a pivoting feature 167 such as a pin or groove on the blade 112, so that the wire is unable to rotate relative to that feature. The back and forth motion of the wire 168, combined with its curved shape cause the inwardly curving portion 169 of the wire towards its distal end 170 to rotate the pivoting feature 167 in the same way that rotating the end of a door handle causes it to rotate around its pivot. In order for this arrangement to be effective, the rigidity of the wire 168 must be sufficiently great that it is able to resist any friction (or other resistance to rotation) between the hole 126 in the blade 112 and the axle on which the blade is mounted. The greater the curvature of the wire 168, and relatedly the greater the length of the inwardly curving portion 169, the more effective this actuation mechanism 160—since there is an improved lever action. This arrangement is advantageous in its simplicity.

Figure 6A:
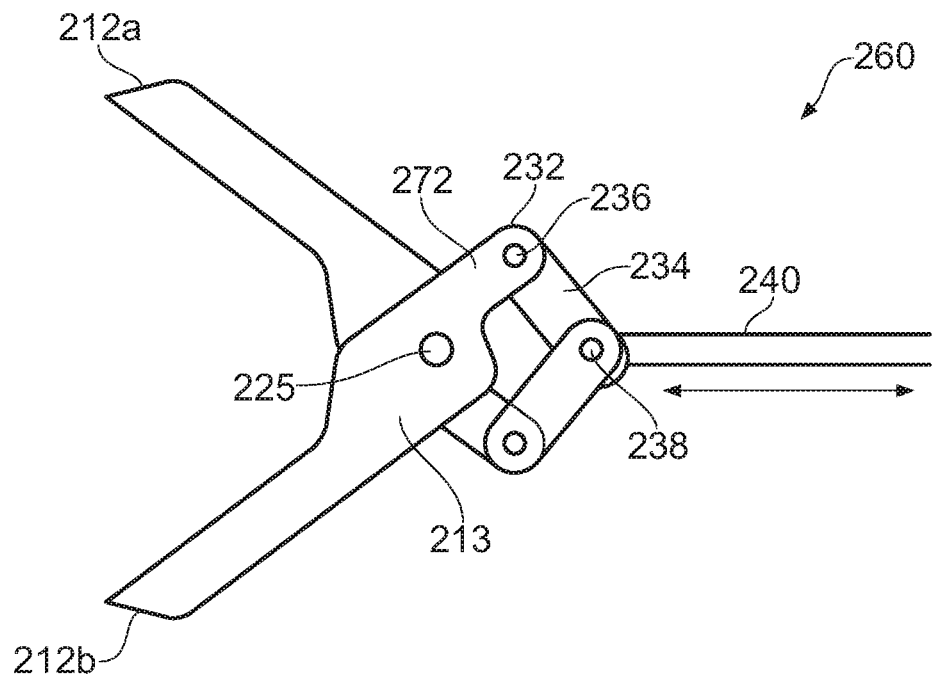
FIGS. 6A and 6B show another actuation mechanism which may be used in embodiments of the present invention.
Figure 6B:
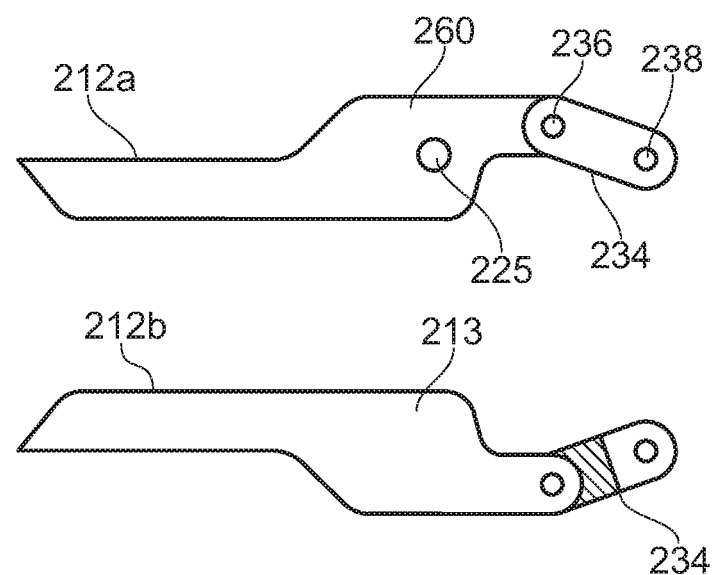

A further alternative actuation mechanism 260 is shown in FIGS. 6A and 6B. In this arrangement, each blade 212a, 212b has a projecting arm 272 that extends rearwardly from a pivot part 213. The proximal end 232 of arm 272 is connected to the distal end of a linkage 234. The linkage 234 and arm 272 are connected pivotably, via a fastener such as a pin 236. The linkage 234 is free to rotate relative to the arm 272, about the pin 236. A proximal end of the linkage 234 is connected pivotably via another pin 238 to the distal end of a central push rod 240. The blades 212a, 212b are connected symmetrically to the push rod 240 via linkages 234a, 234b. This symmetrical arrangement is important since when the blades 212a, 212b are actuated, it helps to ensure that the motion of the push rod 240 is constrained in the direction shown by the arrows, rather than wobbling from side to side.

As in the cam arrangement embodiment described above, the key to this actuation mechanism 260 is relative motion between the pin 238 and the pivot point 225. Additionally, the presence of the arm 272 and the linkage 234 means that the pin 236 must remain at a fixed distance between both the pin 238 and the pivot point 225. Thus, when the push rod 240 is moved forward (i.e. upwards), the angle between the projecting arm 272 and the linkage 234 must decrease to maintain the fixed separation, causing rotation of the arm 272 about the pivot point 225, and accordingly rotation of the whole blade 212a, 212b about the pivot point 225.

FIGS. 7A to 7E are schematic (not to scale) diagrams of the proximal end of the clevis structure 40, which illustrate the electrical connections between the inner 82 and outer 84 conductors of the coaxial transmission line 80 and the electrodes on the surfaces of the first 12a and the second 12b blade. In these schematic diagrams, the actuation mechanisms 60 are omitted though it will be appreciated that the various actuation mechanisms described above are compatible with all of the electrical connection configurations. Likewise, although the blades 12a, 12b are shown adjacent each other with a gap in between, it can be appreciated that the same electrical connections can be using which any blade configuration, e.g. the plier-type or scissor-type arrangements discussed herein.

Figure 7A:
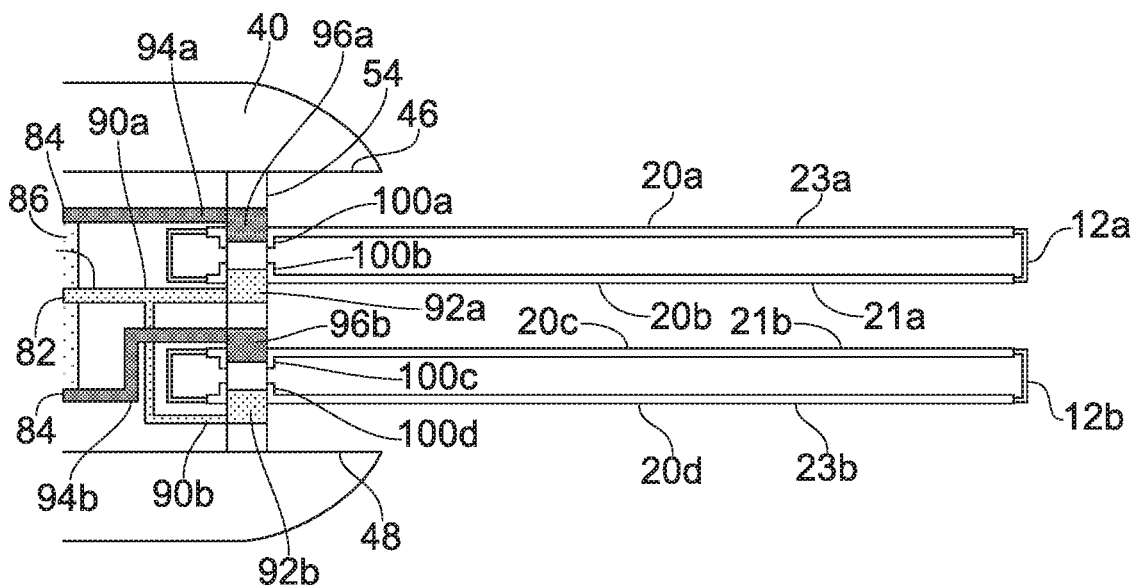
FIGS. 7A to 7E are schematic cross sections showing the electrical connections between the coaxial transmission lines and conductive elements on the blades.

In FIG. 7A, the electrical connections are made via the axle 54. In this way, the electrical connections are formed at the part which moves the least when the blades 12a, 12b rotate. Coaxial transmission line 80 terminates at the base 50 of the recess 44. The inner conductor 82 extends past the end surface 87 of the dielectric material 86 of the coaxial transmission line, into electrical contact 90, which splits into a first branch 90a and a second branch 90b. In this embodiment, electrical contact 90 is an extension of inner conductor 82 and is continuous therewith, however it is possible that electrical contact 90 is formed from a separate piece of conducting material in electrical contact with the end surface 83 of inner conductor 82. First branch 90a extends between the blades 12a, 12b and is in electrical contact with conducting sleeve 92a. Conducting sleeve 92a is in the form of a layer of conducting material coating the outside surface of the axle 54. The position of conducting sleeve 92a with respect to the distal end of the first branch 90a and the first blade 12a is discussed in more detail below.

Second branch 90b extends across the recess, past the proximal end of the second blade 12b (without coming into electrical contact with it), and extends into the region between clevis wall 48 and the outer surface 23a of the second blade 12b. The distal end of second branch 90b, like the first branch 90a, is in electrical contact with conducting sleeve 92b, which has a similar structure to conducting sleeve 92a.

The outer conductor 84 of coaxial transmission line 80 in electrically connected with electrical contacts 94a, 94b. Electrical contact 94a extends into the region between the outer surface 23a of the first blade 12a and clevis wall 46, and is electrically connected to conducting sleeve 96a, which has the same structure as the previously mentioned conducting sleeves 92a, 92b. As with the inner conductor 82, the electrical contact 94a may be continuous with the outer conductor 84 of the coaxial transmission line 80, or it may be formed of a separate piece of conducting material in contact with the end surface 85 of outer conductor 84.

Electrical contact 94b extends into the region between the inner surfaces 21a, 21b of the blades 12a, 12b. In doing so, it is important that it is electrically isolated from electrical contact 90, in order to prevent a short circuit. In practice, this may be achieved either by having an angular offset between the contact 90, 94 within the recess, which is not illustrated in FIG. 7A, or by placing an insulating coating around the electrical contacts 90, 94a, 94b. A distal end of electrical contact 94b is electrically connected to conducting sleeve 96b, which again has a similar structure to the three previously described conducting sleeves 92a, 92b, 94a.

The blades 12a, 12b are mounted on axle 54. Metallization 20a, 20b, 20c, 20d on the surfaces 21a, 21b, 23a, 23b of each blade is shown by the thick black lines in the drawings. This metallization 20a, 20b, 20c, 20d needs to be electrically connected to the coaxial transmission line 80 in order to perform cutting and coagulation using microwave/RF energy. In the embodiment shown in FIG. 7A, the electrical connection is via the axle 54. More specifically, using the first blade 12a as an example (the situation is identical for the second blade 12b), the metallization 20 on e.g. the inner surface 21a of the blade 12a extends over a lip at the circumference of the hole 26 in the blade 12a (through which it is mounted on the axle 54), to form a conducting shell 100a on the inner surface of the hole 26. Then, when the blade 12a is mounted on the axle 54, an electrical connection is formed between the conducting shell 100a and conducting sleeve 92a. Accordingly, in the present embodiment, it is necessary for the conducting sleeve 92a to be located in a position whereby it may be electrically connected to both the distal end of electrical contact 90a and conducting shell 100a. The same applies for the remaining three conducting sleeves 92b, 96a, 96b. In use, as the blades 12a, 12b rotate about the axle 54, using the actuation mechanism 60 (not shown), the circumferential electrical connection between the conducting shell 100a, 100b, 100c, 100d and conducting sleeve 92a, 92b, 96a, 96b is maintained at all points during the rotation, to ensure a uniform signal is delivered to the metallization 20a, 20b, 20c, 20d. In order to ensure the electrical connection is reliable, in the present embodiment, the inner surface of the holes 26a, 26b, i.e. the conducting shells 100a, 100b, 100c, 100d are flush with the outer surface of the axle 54, i.e. the conducting sleeves 92a, 92b, 96a, 96b.

Figure 7B:
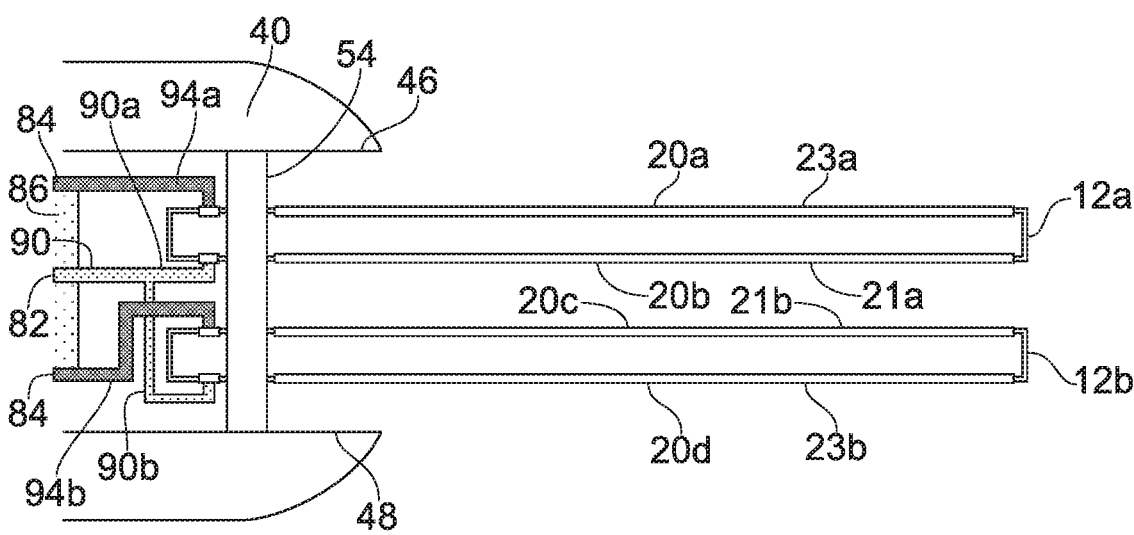

FIG. 7B shows a similar arrangement to FIG. 7A. Features which are unchanged from the previous embodiment are not described again, and are given corresponding reference numerals.

In the embodiment of FIG. 7B, rather than being connected at the axle 54, the distal ends of the electrical contacts 90, 94a, 94b and the branches 90a, 90b are connected to the metallization 20a, 20b, 20c, 20d on the respective surfaces 21a, 21b, 23a, 23b of the blades 12a, 12b directly. In these embodiments, it is essential that there is metallization 20a, 20b, 20c, 20d on all parts of the surfaces 21a, 21b, 23a, 23b of the blades 12a, 12b which the electrical contacts 90, 94a, 94b may contact during rotation of the blades 12a, 12b. This is straightforwardly achieved by having a large portion of the proximal portion of the blade covered in metallization covered, e.g. as shown in FIGS. 5A and 5B. In an alternative embodiment (not shown), the electrical contacts may be electrically connected to the metallization on the surfaces of the blades at a position which is above the axle 54, rather than below, as in FIG. 7B. In such embodiment, the electrical contacts should be electrically isolated from the axle 54 itself.

Figure 7C:
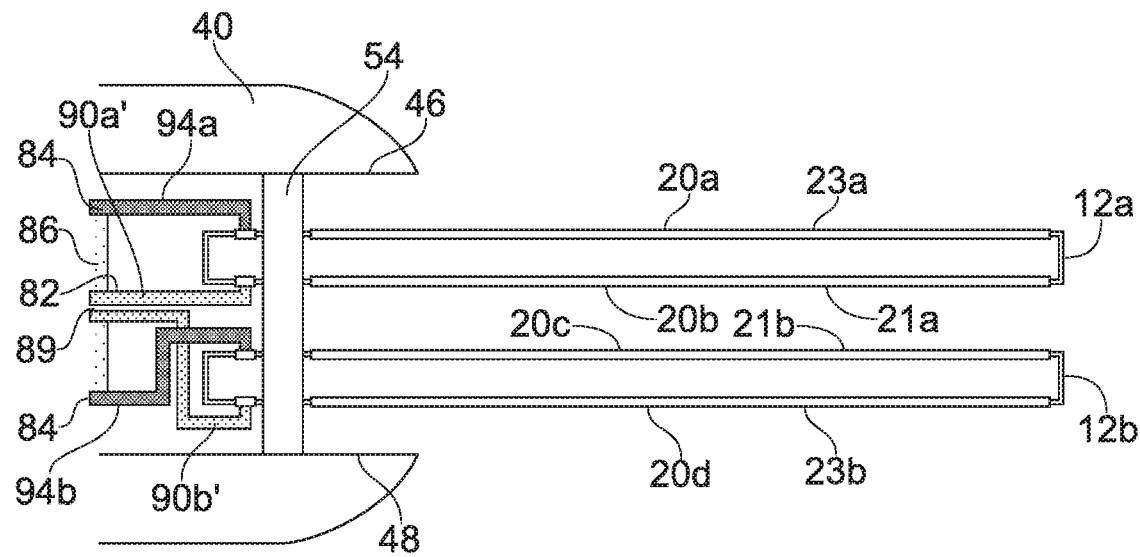

FIG. 7C illustrates an embodiment similar to the previous two, in which the inner conductor 82 of the coaxial transmission line 80 is hollow, to define a channel 89. In this case, rather than having a branched electrical contact, as in FIGS. 7A and 7B, electrical contacts 90a', 90b' extend from opposite sides of the end surface of the inner conductor 82. In the embodiment shown, the distal ends of the electrical contacts 90a', 90b' are electrically connected to the metallization 20b, 20c on the surfaces 21a, 21b of the blades 12a, 12b but in other embodiments, they may be electrically connected to conducting sleeves on the axle 54 as in the embodiment of FIG. 7A.

Figure 7D:
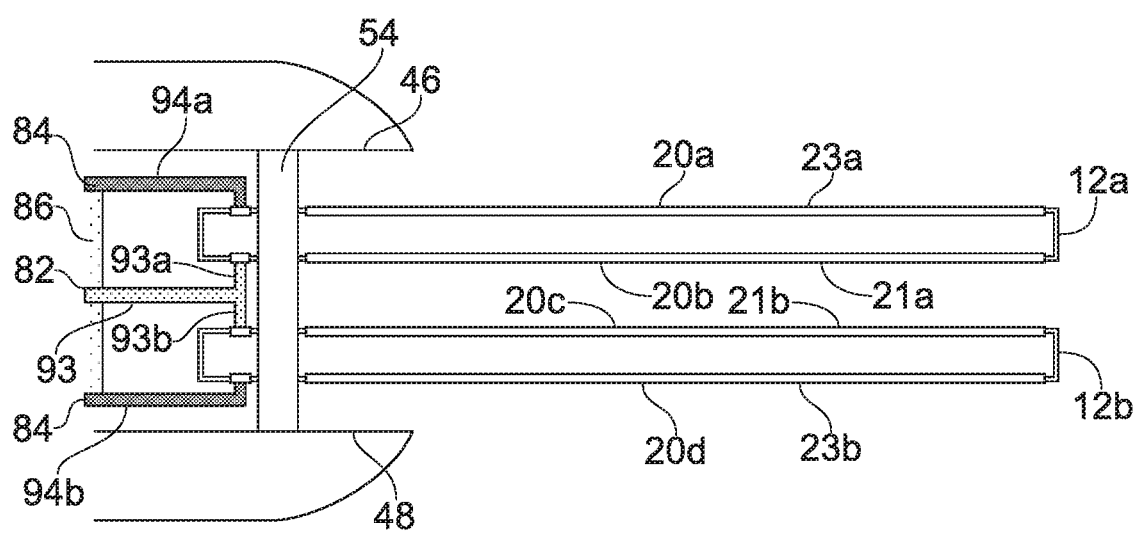

FIG. 7D shows yet another similar embodiment to the previous three drawings. In this case, there is no crossover of the electrical contacts required, since inner conductor 82 is connected to the inner surfaces 21a, 21b of the blades, and outer conductor 84 is connected to the outer surfaces 23a, 23b of the blades. In this particular, example, electrical contact 93 which is continuous with inner conductor branches into a T-shape near the axle 54, with each arm 93a, 93b of the T contacting metallization 20b, 20c on one of the blades 12a, 12b. Of course, a T-shape is one of many shapes which inner conductor could take in embodiments such as this. As has been previously described, this arrangement might be employed in plier-like configurations of the electrosurgical cutting tool, to avoid repulsion between the blades 12a, 12b, illustrated in FIG. 9

Figure 7E:
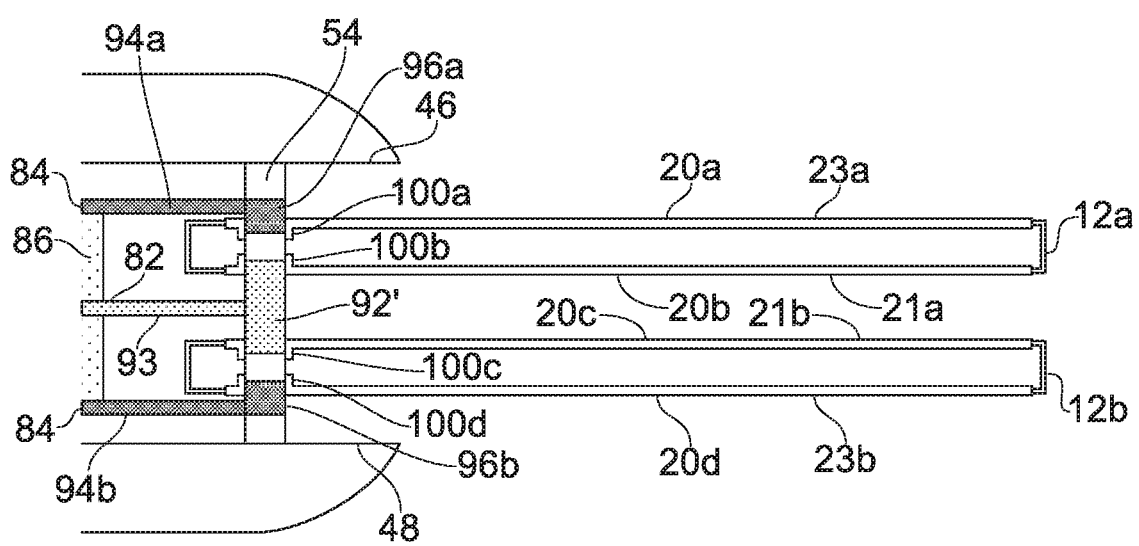

FIG. 7E shows a similar embodiment to the previous, except in this case, the connection with the metallization 20a, 20b, 20c, 20d on the blades 12a, 12b is made via conductive sleeves 92', 96a 96b on the axle 54, as in FIG. 7A. In the present embodiment, there are two conductive sleeves 96a, 96b for connection with electrical contacts 94a, 94b extending from the outer conductor 84 of coaxial transmission line 80, and a single conducting sleeve 92' which connects to the inner surfaces of the holes 26a, 26b in both the blades 12a, 12b and is electrically connected to the inner conductor 82 by a single, unbranched electrical contact 90'. In a similar embodiment (not shown), there may be a conducting sleeve associated with each the inner surfaces of the blades, and electrical contact in this case would branched into e.g. a Y-shape so that distal ends of each of the branches can form an electrical connection with one of the conducting sleeves.

Figure 8:
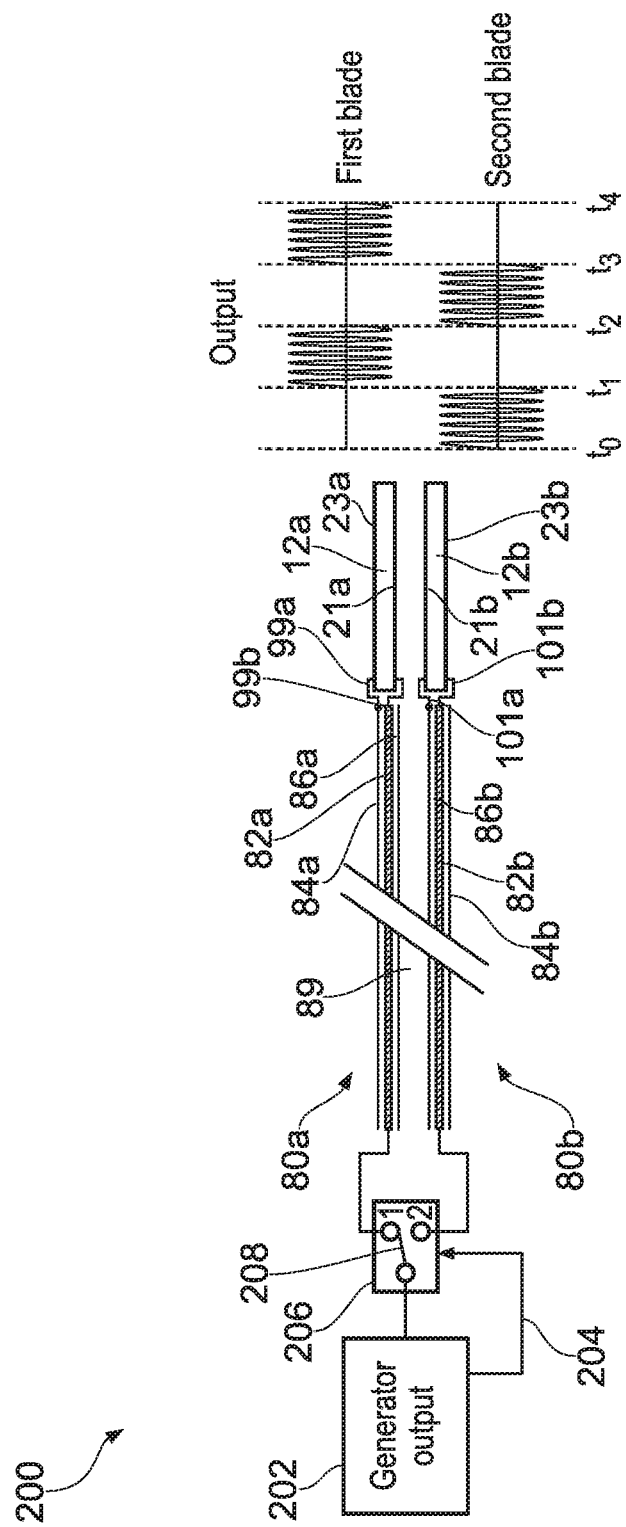
FIG. 8 shows an electrosurgical cutting tool, according to an embodiment of a second aspect of the present invention.

FIG. 8 is a schematic drawing that illustrates an electrosurgical apparatus including the electrosurgical cutting tool 200 according to an embodiment of the second aspect of the present invention. In addition to the cutting tool 200, FIG. 8 also includes a generator output 202 which may supply RF and/or microwave frequency signals to the cutting tool 200. The generator output 202 is connected to SPDT switch 206 via connection 204. SPDT switch 206 has an input terminal and two output terminals (shown as 1 and 2 in FIG. 8). Pole 208 is able to switch rapidly between the two output terminals. Each of the outputs is connected to a single coaxial transmission line, either first coaxial transmission line 80a or second coaxial transmission line 80b. As a result, as pole 208 oscillates between the two output terminals, only one of the coaxial transmission lines 80a, 80b is connected to the generator at any one time. The coaxial transmission lines 80a, 80b are formed of an inner conductor 82a, 82b, an outer conductor 84a, 84b and a dielectric material 86a, 86b separating the two. These transmission lines 80a, 80b may be in the form of standard 50Ω coaxial cables.

A space in between the first coaxial transmission line 80a and the second transmission line 80b forms a channel 89, through which a push rod or guide wire (not shown) may be inserted to act as an actuation means. A simplified schematic of the electrical connections between the coaxial transmission lines 80a, 80b and the first blade 12a and second blade 12b is shown at the distal end of the coaxial transmission lines 80a, 80b. More specifically, the components are connected as follows:

Outer conductor 84a of first coaxial transmission line 80a is connected to outer surface 23a of first blade 12a via connection 99a.

Inner conductor 82a of first coaxial transmission line 80a is connected to inner surface 21a of first blade 12a via connection 99b.

Outer conductor 84b of second coaxial transmission line 80b is connected to inner surface 21b of second blade 12b via connection 101a.

Inner conductor 82b of second coaxial transmission line 80b is connected to outer surface 23b of second blade 12b via connection 101b.

There is metallization (not shown) on the inner and outer surfaces 21a, 21b, 23a, 23b of both blades 12a, 12b, to form the first and second electrodes, as previously discussed. Please note that in this schematic drawing, features such as the clevis 40 and the axle 54 are omitted in order not to obscure other features of the cutting tool 200, though these are fully compatible with the embodiment shown. For example, the connections between the coaxial transmission lines 80a, 80b and the blades 12a, 12b may also be formed using similar structures to those shown in FIGS. 7A to 7E.

FIG. 8 also shows a plot of the output of each blade. As the pole 208 oscillates within the SPDT switch 206, the generator output 202 is alternately supplied, in turn, to the first blade 12a and the second blade 12b. The pole 208 switches position at times $t_i$ (i=0, 1, 2, 3, 4), as can be seen from the plots. At no point is there a signal being output from both blades 12a, 12b simultaneously. In a preferred embodiment the switching interval of the throw is approximately 20 ms. It should be noted that the waveforms are drawn schematically to illustrate when a signal is being received at the blades 12a, 12b. In reality, the waveform itself would have a much higher frequency, even at the lowest end of the RF spectrum. The waveforms shown in FIG. 8 should not be taken as representative of the frequencies employed in embodiments of the present invention.

Figure 9:
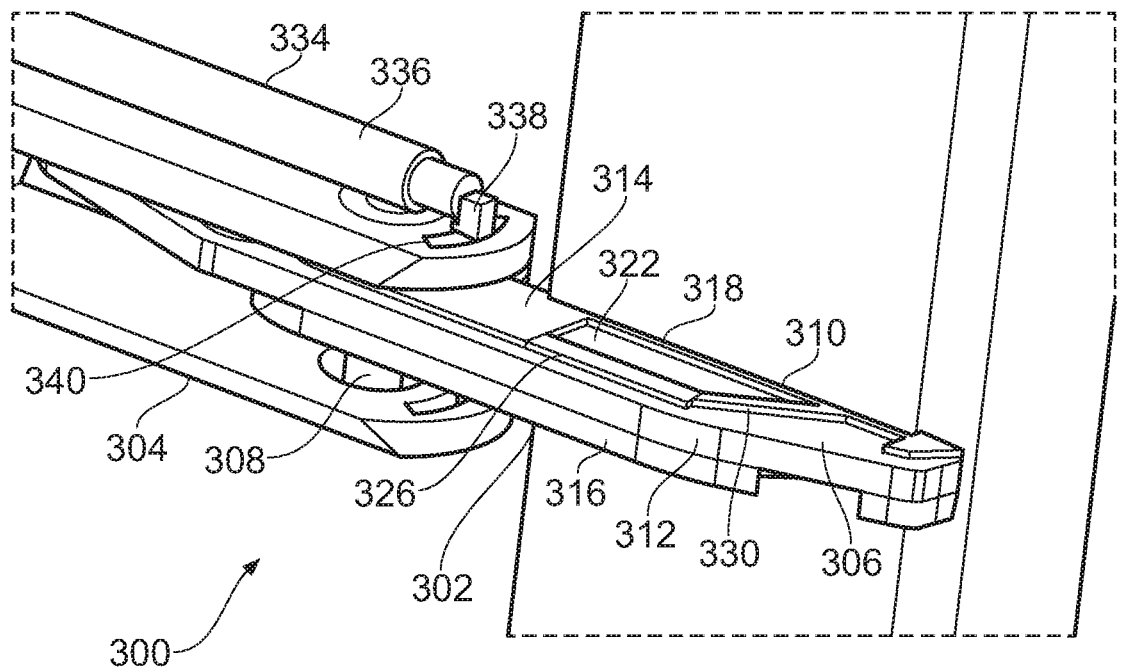
FIG. 9 is a top perspective view of a simulated blade structure for a cutting tool that is an embodiment of the invention.
Figure 10:
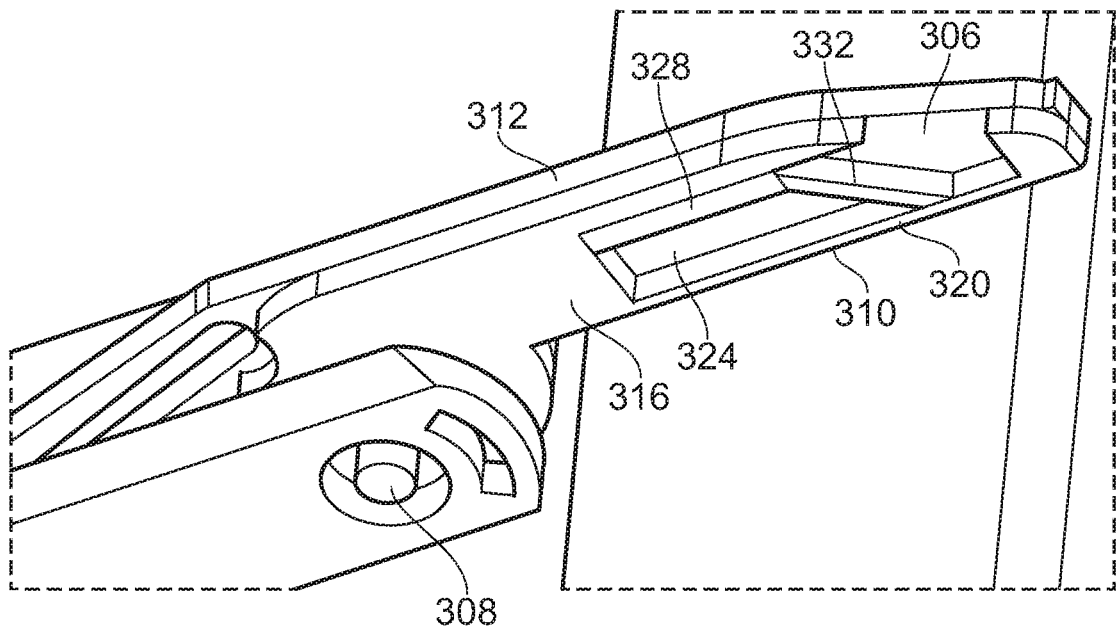
FIG. 10 is a bottom perspective view of the blade structure shown in FIG. 9.

FIGS. 9 and 10 are upper and lower views of a schematic blade structure 300 that can be used in a cutting tool that is an embodiment of the invention. Although only one blade 302 is shown in FIG. 9, it can be appreciated that the illustrated clevis structure 304 leaves room for a second blade to be mounted adjacent the blade 302 such that they operate in a scissor-like manner.

In this embodiment, the blade 302 comprises a planar dielectric element 306 that is pivotably mounted to the clevis structure 304 about an axle 308. The planar dielectric element 306 has an inward flat edge 310 for engaging biological tissue, and an outward curved edge 312 opposite to the inward flat edge 310.

A first conductive element 314 is mounted on an upper surface of the planar dielectric element 306. A second conductive element 316 is mounted on a lower surface of the planar dielectric element 306. In this embodiment, the first and second conductive elements 314, 316 is a patterned layer of metallisation on the upper surface. The patterns and thicknesses for the first and second conductive elements can be chosen (e.g. using simulations) to ensure an uniform delivery of microwave power along the inward flat edge.

In this embodiment, the first conductive element 314 is set back from the outward curved edge 312, whereas the second conductive element extends to meet the outward curved edge 312. Both the first and second conductive elements 314, 316 extend to meet (and may be exposed at) the inward flat edge 310. The second conductive element 316 may have a greater thickness than the first conductive element 314. Each of the first and second conductive elements 314, 316 may have a respective finger of metallisation 318, 320 that extends along the inward flat edge 310 and a respective cut out portion 322, 324 where no metallisation is present behind the finger of metallisation. Each cut out portion 322, 324 may be bounded by a outward strip of metallisation 326, 328, which is electrically connected to its respective finger of metallisation 318, 320 by an angled connecting strip 330, 332. This configuration improves the return loss of the blade structure and also ensures even power delivery, as discussed below.

In the arrangement shown in FIGS. 9 and 10, power is delivered to the blade structure 300 by a coaxial cable 334 mounted on the outside of the clevis structure 304. A second coaxial cable (not shown) on the other side of the clevis structure may be used to provide power to a second blade.

The coaxial cable 334 has an outer conductor 336 that is electrically connected to the axle 308, which in turn is electrically connected to the second conductive element 316. The coaxial cable 334 has an inner conductor that protrudes beyond a distal end of the outer conductor 336 to electrically connect to a laterally extending coupling block 338 which passes through a hole 340 in the clevis structure 304 to electrically connect to the first conductive element 314.

Figure 11:
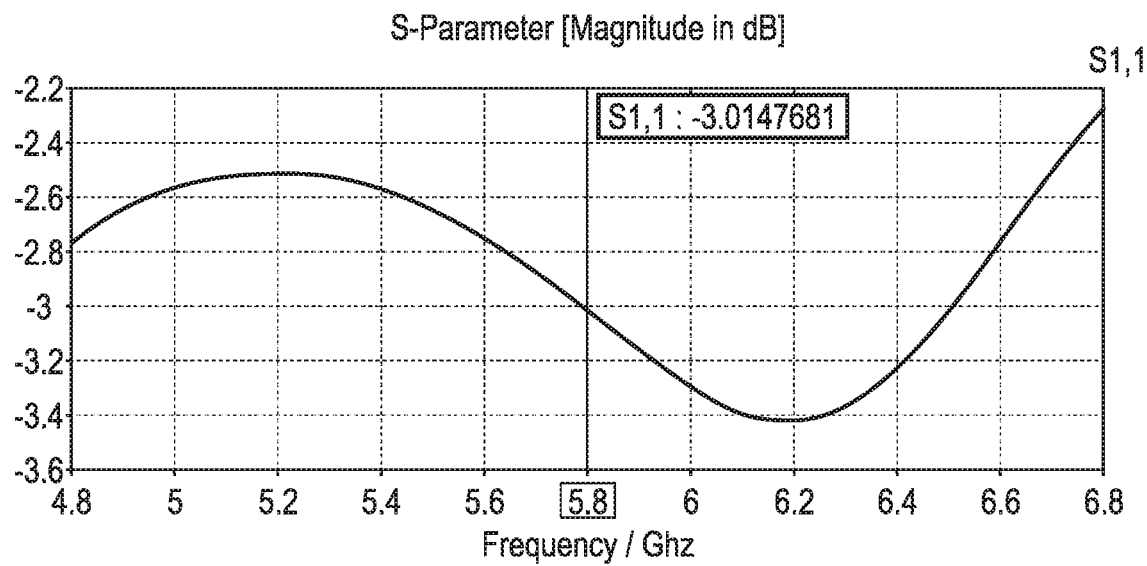
FIG. 11 is a graph showing return loss for the blade structure shown in FIG. 9 when delivering microwave energy in to biological tissue.

FIG. 11 is a graph showing return loss of the blade structure 300. When microwave energy having a frequency of 5.8 GHz is supplied through the coaxial cable 334, the return loss is better than 3 dB.

Figure 12:
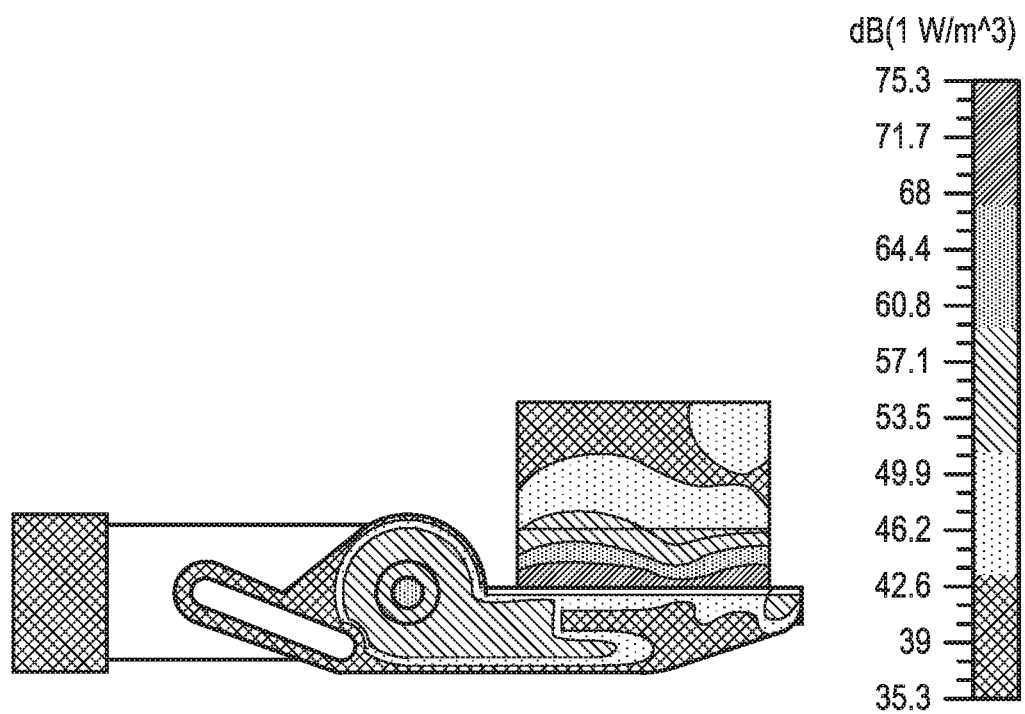
FIG. 12 is a power density simulation for the blade structure shown in FIG. 9 when in contact with biological tissue.

FIG. 12 is a simulation of the blade structure 300 that showing power absorption into biological tissue for microwave energy having a frequency of 5.8 GHz. It can be seen that there is a region of uniform power delivery adjacent to the inward flat edge, without any significant unwanted power leakage from other areas of the blade.

The invention claimed is:

1. An electrosurgical cutting tool comprising:
a first blade and a second blade, joined at a pivot point, with the first blade comprising a planar body made of a first dielectric material separating a first conductive element on a first surface thereof from a second conductive element on a second surface thereof, the second surface facing in an opposite direction to the first surface;
actuation means for causing relative rotation between the first blade and the second blade about the pivot point to cause a gap between the first blade and the second blade to change between an open position and a closed position, the relative rotation being substantially in a plane of the first blade and the second blade; and
a coaxial transmission line for delivering radio frequency (RF) energy and microwave energy to the first blade, the coaxial transmission line having an inner conductor and an outer conductor separated by a second dielectric material,
wherein the inner conductor and the outer conductor are each connected to one of the first conductive element and the second conductive element of the first blade,
wherein the first conductive element and the second conductive element of the first blade are able to act as active and return electrodes for sustaining an RF electric field therebetween, the RF electric field corresponding to the RF energy delivered to the first blade by the coaxial transmission line,
wherein the first conductive element and the second conductive element of the first blade are able also to act as an antenna structure for radiating a microwave electromagnetic (EM) field corresponding to the microwave energy delivered to the first blade by the coaxial transmission line,
wherein the first blade and the second blade are mounted in a clevis structure which is located at a distal end of the electrosurgical cutting tool, the clevis structure comprising a base for attaching to the coaxial transmission line, and a housing that defines a longitudinal recess for receiving the first blade and the second blade,
wherein the clevis structure comprises an axle that traverses the longitudinal recess, and wherein the first blade and the second blade are rotatably mounted on the axle, and
wherein electrical connections between the inner conductor and the outer conductor of the coaxial transmission line and the first conductive element and the second conductive element on the first blade are made via conductive sleeves on the axle.

2. The electrosurgical cutting tool according to claim 1, wherein the second blade comprises a planar body made of a first dielectric material separating the first conductive element on a first surface thereof from the second conductive element on a second surface thereof, the second surface facing in an opposite direction to the first surface,
wherein:
the coaxial transmission line is arranged to deliver the RF energy and the microwave energy to the second blade;
the inner conductor and the outer conductor are each connected to one of the first conductive element and the second conductive element of the second blade;
the first conductive element and the second conductive element of the second blade are able to act as active and return electrodes for sustaining an RF electric field therebetween, the RF electric field corresponding to the RF energy delivered to the second blade by the coaxial transmission line; and
the first conductive element and the second conductive element of the second blade are able also to act as an antenna structure for radiating a microwave EM field corresponding to the microwave energy delivered to the second blade by the coaxial transmission line.

3. The electrosurgical cutting tool according to claim 2, wherein the first conductive element of the first blade and the second conductive element of the second blade are exposed on faces of the first blade and the second blade that oppose each other across the gap.

4. The electrosurgical cutting tool according to claim 3, wherein the faces of the first blade and the second blade that are opposed across the gap are oriented perpendicularly to the plane of the first blade and the second blade.

5. The electrosurgical cutting tool according to claim 2, wherein:
the inner conductor of the coaxial transmission line is electrically connected to the first conductive element of the first blade and to the second conductive element of the second blade, and
the outer conductor of the coaxial transmission line is electrically connected to the second conductive element of the first blade and the first conductive element of the second blade.

6. The electrosurgical cutting tool according to claim 2, wherein:
the inner conductor of the coaxial transmission line is electrically connected to the first conductive element of the first blade and to the first conductive element of the second blade, and
the outer conductor of the coaxial transmission line is electrically connected to the second conductive element of the first blade and the second conductive element of the second blade.

7. The electrosurgical cutting tool according to claim 2, wherein during movement from the open position to the closed position, the first surface of the first blade and the first surface of the second blade slide past each other.

8. The electrosurgical cutting tool according to claim 2, wherein, in the closed position, faces of the first blade and the second blade that oppose each other across the gap are parallel.

9. The electrosurgical cutting tool according to claim 1, wherein the first conductive element and the second conductive element are formed from one or more layers of metallization on the first surface and second surface.

10. The electrosurgical cutting tool according to claim 1, wherein a thickness of the first dielectric material is equal to or less than 1 millimeter (mm).

11. The electrosurgical cutting tool according to claim 1, wherein, when in the closed position, the electrosurgical cutting tool has an maximum outer diameter equal to or less than 5 millimeter (mm).

12. The electrosurgical cutting tool according to claim 1, wherein the inner conductor of the coaxial transmission line is hollow, and defines a channel running therethrough.

13. The electrosurgical cutting tool according to claim 1, wherein the actuation means comprises an actuation element that is movable relative to the pivot point.

14. The electrosurgical cutting tool according to claim 13, wherein the actuation element comprises a push rod that is operably connected to the first blade and/or the second blade.

15. The electrosurgical cutting tool according to claim 1, wherein the actuation means comprises a cam arrangement.

16. The electrosurgical cutting tool according to claim 15, wherein the cam arrangement comprises:
    a push rod mounted to slide longitudinally with respect to the pivot point; and
    a guide path formed on the first blade,
        wherein the push rod is operably engaged with the guide path, and
        wherein the guide path is offset from a longitudinal direction, whereby longitudinal movement of the push rod relative to the pivot point causes the first blade to pivot with respect to the pivot point.

17. The electrosurgical cutting tool according to claim 16, wherein the guide path is a linear track extending in a direction that is offset from the pivot point.

18. The electrosurgical cutting tool according to claim 17, wherein the push rod comprises a follower mounted in and constrained to lie on the linear track.

19. The electrosurgical cutting tool according to claim 16, wherein the push rod is slidably mounted on the coaxial transmission line.

20. The electrosurgical cutting tool according to claim 14, wherein the actuation means comprises a linkage having a proximal end pivotably connected to the push rod and a distal end pivotably connected to the first blade at a location offset from the pivot point.

21. The electrosurgical cutting tool according to claim 14, wherein the push rod comprises a wire having a preformed curved distal portion that is rigidly secured to the first blade.

22. The electrosurgical cutting tool according to claim 1, further comprising a biasing means arranged to urge the first blade and the second blade towards the open position.

23. An electrosurgical cutting tool comprising:
    a first blade and a second blade joined at a pivot point, each blade comprising a planar body made of a first dielectric material separating a first conductive element on a first surface from a second conductive element on a second surface, the second surface facing in an opposite direction to the first surface;
    actuation means for causing relative rotation between the first blade and the second blade about the pivot point, between and open position and a closed position, the relative rotation being substantially in a plane of the first blade and the second blade;
    a first coaxial transmission line having a first inner conductor and a first outer conductor separated by a second dielectric material, the first coaxial transmission line arranged to deliver radio frequency (RF) and microwave frequency signals for the first blade, wherein the first inner conductor and the first outer conductor are respectively connected to the first conductive element and the second conductive element of the first blade; and
    a second coaxial transmission line having a second inner conductor and a second outer conductor separated by a third dielectric material, the second coaxial transmission line arranged to deliver RF and microwave frequency signals to the second blade, wherein the second inner conductor and the second outer conductor are respectively connected to the first conductive element and the second conductive element of the second blade, wherein:
        the first conductive element and the second conductive element of each blade of the first blade and the second blade are able to act as active and return electrodes for sustaining an RF electric field therebetween, the RF electric field corresponding to the RF signal delivered to the first blade and the second blade by the first coaxial transmission line and the second coaxial transmission line respectively,
        the first conductive element and the second conductive element are able also to act as an antenna structure for radiating a microwave frequency electromagnetic (EM) field corresponding to the microwave frequency signal delivered to the first blade and the second blade by the first coaxial transmission line and the second coaxial transmission line respectively,
        the first blade and the second blade are mounted in a clevis structure which is located at a distal end of the electrosurgical cutting tool, the clevis structure comprising a base for attaching to the first coaxial transmission line and the second coaxial transmission line, and a housing that defines a longitudinal recess for receiving the first blade and the second blade,
        the clevis structure comprises an axle that traverses the longitudinal recess, and wherein the first blade and the second blade are rotatably mounted on the axle, and
        electrical connections between the first inner conductor and the first outer conductor of the first coaxial transmission line and the first conductive element and the second conductive element of the first blade and the second inner conductor and the second outer conductor of the second coaxial transmission line and the first conductive element and the second conductive element of the second blade are made via conductive sleeves on the axle.

24. An electrosurgical apparatus comprising:
an electrosurgical generator arranged to output the RF energy and the microwave energy; and
the electrosurgical cutting tool according to claim 1 connected to receive the RF energy and the microwave energy from the electrosurgical generator.

25. The electrosurgical apparatus according to claim 24, further comprising a signal alternator arranged to alternately switch the RF energy or the microwave energy from the electrosurgical generator between the first blade and the second blade.

26. The electrosurgical apparatus according to claim 25, wherein the signal alternator comprises any one of a co-axial switch, PIN diode, and varactor diode power switch.

\* \* \* \* \*